(12) United States Patent
Longo

(10) Patent No.: US 10,245,167 B2
(45) Date of Patent: Apr. 2, 2019

(54) DELIVERY DEVICE AND METHOD OF DELIVERY

(71) Applicant: Intact Vascular, Inc., Wayne, PA (US)

(72) Inventor: Michael Longo, Glenmoore, PA (US)

(73) Assignee: Intact Vascular, Inc., Wayne, PA (US)

( * ) Notice: Subject to any disclaimer, the term of this patent is extended or adjusted under 35 U.S.C. 154(b) by 233 days.

(21) Appl. No.: 15/227,757

(22) Filed: Aug. 3, 2016

(65) Prior Publication Data

US 2017/0000633 A1  Jan. 5, 2017

Related U.S. Application Data

(63) Continuation of application No. 15/000,437, filed on Jan. 19, 2016, now Pat. No. 9,433,520.
(Continued)

(51) Int. Cl.
*A61F 2/82* (2013.01)
*A61F 2/95* (2013.01)
(Continued)

(52) U.S. Cl.
CPC ............ *A61F 2/958* (2013.01); *A61B 17/068* (2013.01); *A61B 17/10* (2013.01); *A61F 2/844* (2013.01);
(Continued)

(58) Field of Classification Search
CPC ....... A61B 17/068; A61B 17/10; A61F 2/844; A61F 2/915; A61F 2/958; A61F 2/966;
(Continued)

(56) References Cited

U.S. PATENT DOCUMENTS

| 3,051,172 A | 8/1962 | Bruchhaus |
| 3,221,746 A | 12/1965 | Noble |

(Continued)

FOREIGN PATENT DOCUMENTS

| AU | 2008335140 | 11/2012 |
| AU | 2011274392 | 11/2013 |

(Continued)

OTHER PUBLICATIONS

English translation of the first Office Action and Search Report in Chinese Application No. 201610546800.2 in 5 pages dated Sep. 28, 2017.
(Continued)

*Primary Examiner* — Jocelin C Tanner
(74) *Attorney, Agent, or Firm* — Knobbe Martens Olson & Bear, LLP

(57) ABSTRACT

A delivery device can provide sequential delivery of a plurality of intraluminal devices or tacks held in a compressed state on the delivery device. Delivery platforms on the delivery device can hold a tack in a compressed position and be positioned between annular pusher bands that may also be radiopaque markers. The annular pusher bands can be made of wire or sections of material to increase flexibility while remaining radiopacity. A post deployment dilation device can be included. The post deployment dilation device can be a plurality of expansion filaments, a bellows, or a balloon. A tack deployment method can include allowing a self-expanding tack to expand, aligning the post deployment dilation device under the tack, and causing the post deployment dilation device to expand radial to push outward on the tack.

26 Claims, 16 Drawing Sheets

Related U.S. Application Data

(60) Provisional application No. 62/109,550, filed on Jan. 29, 2015, provisional application No. 62/109,534, filed on Jan. 29, 2015, provisional application No. 62/274,236, filed on Jan. 1, 2016.

(51) Int. Cl.
*A61B 17/10* (2006.01)
*A61F 2/844* (2013.01)
*A61F 2/915* (2013.01)
*A61F 2/958* (2013.01)
*A61F 2/966* (2013.01)
*A61M 29/00* (2006.01)
*A61B 17/068* (2006.01)

(52) U.S. Cl.
CPC .............. *A61F 2/915* (2013.01); *A61F 2/966* (2013.01); *A61M 29/00* (2013.01); *A61F 2002/826* (2013.01); *A61F 2002/91566* (2013.01); *A61F 2002/91583* (2013.01); *A61F 2002/9511* (2013.01); *A61F 2210/0014* (2013.01); *A61F 2250/0098* (2013.01)

(58) Field of Classification Search
CPC ...... A61F 2002/826; A61F 2002/91566; A61F 2002/91583; A61F 2002/9511; A61F 2210/0014; A61F 2210/0098; A61M 29/00
See application file for complete search history.

(56) References Cited

U.S. PATENT DOCUMENTS

| | | |
|---|---|---|
| 3,635,223 A | 1/1972 | Klieman |
| 4,024,873 A * | 5/1977 | Antoshkiw ............ A61B 5/028 604/101.04 |
| 4,292,974 A | 10/1981 | Fogarty et al. |
| 4,446,867 A | 5/1984 | Leveen et al. |
| 4,465,072 A | 8/1984 | Taheri |
| 4,515,587 A | 5/1985 | Schiff |
| 4,545,367 A | 10/1985 | Tucci |
| 4,545,390 A | 10/1985 | Leary |
| 4,552,127 A | 11/1985 | Schiff |
| 4,576,591 A | 3/1986 | Kay et al. |
| 4,589,412 A | 5/1986 | Kensey |
| 4,641,654 A | 2/1987 | Samson et al. |
| 4,651,738 A | 3/1987 | Demer et al. |
| 4,687,465 A | 8/1987 | Prindle et al. |
| 4,723,550 A | 2/1988 | Bales et al. |
| 4,723,936 A | 2/1988 | Buchbinder et al. |
| 4,723,938 A | 2/1988 | Goodin et al. |
| 4,726,374 A | 2/1988 | Bales et al. |
| 4,758,223 A | 7/1988 | Rydell |
| 4,762,130 A | 8/1988 | Fogarty et al. |
| 4,781,192 A | 11/1988 | Demer |
| 4,784,636 A | 11/1988 | Rydell |
| 4,846,174 A | 7/1989 | Willard et al. |
| 4,848,342 A | 7/1989 | Kaltenbach |
| RE33,166 E | 2/1990 | Samson |
| 4,921,484 A | 5/1990 | Hillstead |
| 4,994,065 A | 2/1991 | Gibbs et al. |
| 5,009,659 A | 4/1991 | Hamlin et al. |
| 5,024,668 A | 6/1991 | Peters et al. |
| 5,042,707 A | 8/1991 | Taheri |
| 5,047,015 A | 9/1991 | Foote et al. |
| 5,102,390 A | 4/1992 | Crittenden et al. |
| 5,160,341 A | 11/1992 | Brenneman et al. |
| 5,190,058 A | 3/1993 | Jones et al. |
| 5,196,024 A | 3/1993 | Barath |
| 5,201,757 A | 4/1993 | Heyn et al. |
| 5,242,452 A | 9/1993 | Inoue |
| 5,246,420 A | 9/1993 | Kraus et al. |
| 5,250,029 A | 10/1993 | Lin et al. |
| 5,250,060 A | 10/1993 | Carbo et al. |
| 5,261,878 A | 11/1993 | Galindo |
| 5,263,962 A | 11/1993 | Johnson et al. |
| 5,269,758 A | 12/1993 | Taheri |
| 5,304,121 A | 4/1994 | Sahatjian |
| 5,318,529 A | 6/1994 | Kontos |
| 5,336,234 A | 8/1994 | Virgil et al. |
| 5,344,397 A | 9/1994 | Heaven et al. |
| 5,383,890 A | 1/1995 | Miraki et al. |
| 5,397,305 A | 3/1995 | Kawula et al. |
| 5,397,355 A | 3/1995 | Marin et al. |
| 5,421,955 A | 6/1995 | Lau et al. |
| 5,423,851 A | 6/1995 | Samuels |
| 5,423,885 A | 6/1995 | Williams |
| 5,443,477 A | 8/1995 | Marin et al. |
| 5,489,295 A | 2/1996 | Piplani et al. |
| 5,501,689 A | 3/1996 | Green et al. |
| 5,534,007 A | 7/1996 | St. Germain et al. |
| 5,536,252 A | 7/1996 | Imran et al. |
| 5,540,659 A | 7/1996 | Teirstein |
| 5,545,135 A | 8/1996 | Iacob et al. |
| 5,562,728 A | 10/1996 | Lazarus et al. |
| 5,569,272 A | 10/1996 | Reed et al. |
| 5,571,135 A | 11/1996 | Fraser et al. |
| 5,591,197 A | 1/1997 | Orth et al. |
| 5,593,417 A | 1/1997 | Rhodes |
| 5,601,568 A | 2/1997 | Chevillon et al. |
| 5,616,149 A | 4/1997 | Barath |
| 5,618,300 A | 4/1997 | Marin et al. |
| 5,632,771 A * | 5/1997 | Boatman ................ A61F 2/885 606/198 |
| 5,634,928 A | 6/1997 | Fischell et al. |
| 5,643,312 A | 7/1997 | Fischell et al. |
| 5,645,559 A | 7/1997 | Hachtman et al. |
| 5,665,116 A | 9/1997 | Chaisson et al. |
| 5,681,346 A | 10/1997 | Orth et al. |
| 5,704,913 A | 1/1998 | Abele et al. |
| 5,707,376 A | 1/1998 | Kavteladze et al. |
| 5,725,572 A | 3/1998 | Lam et al. |
| 5,728,158 A | 3/1998 | Lau et al. |
| 5,741,270 A | 4/1998 | Hansen et al. |
| 5,743,874 A | 4/1998 | Fischell et al. |
| 5,746,716 A | 5/1998 | Vigil et al. |
| 5,746,764 A | 5/1998 | Green et al. |
| 5,776,161 A | 7/1998 | Globerman |
| 5,797,951 A | 8/1998 | Mueller |
| 5,800,526 A | 9/1998 | Anderson et al. |
| 5,807,398 A | 9/1998 | Shaknovich |
| 5,813,977 A | 9/1998 | Hinchliffe et al. |
| 5,817,152 A | 10/1998 | Birdsall et al. |
| 5,833,694 A | 11/1998 | Poncet |
| 5,843,033 A | 12/1998 | Ropiak |
| 5,843,090 A | 12/1998 | Schuetz |
| 5,911,725 A | 6/1999 | Boury |
| 5,925,038 A | 7/1999 | Panescu et al. |
| 5,925,061 A | 7/1999 | Ogi et al. |
| 5,928,247 A | 7/1999 | Barry et al. |
| 5,944,727 A | 8/1999 | Ahari et al. |
| 5,954,742 A | 9/1999 | Osypka |
| 5,957,949 A | 9/1999 | Leonhardt et al. |
| 5,968,052 A | 10/1999 | Sullivan, III et al. |
| 5,968,068 A | 10/1999 | Dehdashtian et al. |
| 5,968,088 A | 10/1999 | Hansen et al. |
| 5,972,023 A | 10/1999 | Tanner et al. |
| 5,980,552 A | 11/1999 | Pinchasik et al. |
| 6,004,328 A | 12/1999 | Solar |
| 6,007,543 A | 12/1999 | Ellis et al. |
| 6,009,614 A | 1/2000 | Morales |
| 6,013,854 A | 1/2000 | Moriuchi |
| 6,036,725 A | 3/2000 | Avellanet |
| 6,048,360 A | 4/2000 | Khosravi et al. |
| 6,053,941 A | 4/2000 | Lindenberg et al. |
| 6,053,943 A | 4/2000 | Edwin et al. |
| 6,080,177 A | 6/2000 | Igaki |
| 6,090,135 A | 7/2000 | Plaia et al. |
| 6,102,904 A | 8/2000 | Vigil et al. |
| 6,110,198 A | 8/2000 | Fogarty et al. |
| 6,123,722 A | 9/2000 | Fogarty et al. |
| 6,126,685 A | 10/2000 | Lenker et al. |

(56) References Cited

U.S. PATENT DOCUMENTS

| | | |
|---|---|---|
| 6,129,754 A | 10/2000 | Kanesaka et al. |
| 6,139,573 A | 10/2000 | Sogard et al. |
| 6,143,016 A | 11/2000 | Bleam et al. |
| 6,146,358 A | 11/2000 | Rowe |
| 6,152,937 A | 11/2000 | Peterson et al. |
| 6,157,852 A | 12/2000 | Selmon et al. |
| 6,165,199 A | 12/2000 | Barbut |
| 6,187,034 B1 | 2/2001 | Frantzen |
| 6,197,013 B1 | 3/2001 | Reed |
| 6,197,103 B1 | 3/2001 | Davies et al. |
| 6,200,336 B1 | 3/2001 | Pavcnik et al. |
| 6,203,550 B1 | 3/2001 | Olson |
| 6,203,568 B1 | 3/2001 | Lombardi et al. |
| 6,203,569 B1 | 3/2001 | Wijay |
| 6,221,102 B1 | 4/2001 | Baker et al. |
| 6,238,402 B1 | 5/2001 | Sullivan et al. |
| 6,241,667 B1 | 6/2001 | Vetter et al. |
| 6,254,628 B1 | 7/2001 | Wallace et al. |
| 6,258,117 B1 | 7/2001 | Camrud et al. |
| 6,266,550 B1 | 7/2001 | Selmon et al. |
| 6,270,524 B1 | 8/2001 | Kim |
| 6,273,909 B1 | 8/2001 | Kugler et al. |
| 6,290,728 B1 | 9/2001 | Phelps et al. |
| 6,312,444 B1 | 11/2001 | Barbut |
| 6,312,460 B2 | 11/2001 | Drasler et al. |
| 6,325,824 B2 | 12/2001 | Limon |
| 6,338,739 B1 | 1/2002 | Datta et al. |
| 6,344,053 B1 | 2/2002 | Boneau |
| 6,364,901 B1 | 4/2002 | Inoue |
| 6,364,904 B1 | 4/2002 | Smith |
| 6,371,962 B1 | 4/2002 | Ellis et al. |
| 6,387,113 B1 | 5/2002 | Hawkins et al. |
| 6,391,050 B1 | 5/2002 | Broome |
| 6,402,760 B1 | 6/2002 | Fedida |
| 6,409,863 B1 | 6/2002 | Williams et al. |
| 6,425,915 B1 | 7/2002 | Khosravi et al. |
| 6,428,550 B1 | 8/2002 | Vargas et al. |
| 6,428,566 B1 | 8/2002 | Holt |
| 6,458,151 B1 | 10/2002 | Saltiel |
| 6,475,237 B2 | 11/2002 | Drasler et al. |
| 6,485,510 B1 | 11/2002 | Camrud et al. |
| 6,491,707 B2 | 12/2002 | Makower et al. |
| 6,508,822 B1 | 1/2003 | Peterson et al. |
| 6,514,261 B1 | 2/2003 | Randall et al. |
| 6,517,573 B1 | 2/2003 | Pollock et al. |
| 6,520,934 B1 | 2/2003 | Lee et al. |
| 6,520,983 B1 | 2/2003 | Colgan et al. |
| 6,527,800 B1 | 3/2003 | McGuckin, Jr. et al. |
| 6,547,817 B1 | 4/2003 | Fischell et al. |
| 6,551,353 B1 | 4/2003 | Baker et al. |
| 6,599,296 B1 | 7/2003 | Gillick et al. |
| 6,602,226 B1 | 8/2003 | Smith et al. |
| 6,607,551 B1 | 8/2003 | Sullivan et al. |
| 6,648,911 B1 | 11/2003 | Sirhan et al. |
| 6,660,031 B2 | 12/2003 | Tran et al. |
| 6,676,698 B2 | 1/2004 | McGuckin, Jr. et al. |
| 6,692,504 B2 | 2/2004 | Kurz et al. |
| 6,699,274 B2 | 3/2004 | Stinson |
| 6,699,277 B1 | 3/2004 | Freidberg et al. |
| 6,706,061 B1 | 3/2004 | Fischell et al. |
| 6,716,240 B2 | 4/2004 | Fischell et al. |
| 6,719,775 B2 | 4/2004 | Slaker et al. |
| 6,723,119 B2 | 4/2004 | Pinchasik et al. |
| 6,730,116 B1 | 5/2004 | Wolinsky et al. |
| 6,746,475 B1 | 6/2004 | Rivelli, Jr. |
| 6,752,828 B2 | 6/2004 | Thornton |
| 6,755,854 B2 | 6/2004 | Gillick et al. |
| 6,786,922 B2 | 9/2004 | Schaeffer |
| 6,790,221 B2 | 9/2004 | Monroe et al. |
| 6,790,227 B2 | 9/2004 | Burgermeister |
| 6,810,882 B2 | 11/2004 | Langberg et al. |
| 6,814,752 B1 | 11/2004 | Chuter |
| 6,827,731 B2 | 12/2004 | Armstrong et al. |
| 6,843,400 B1 | 1/2005 | Lee |
| 6,846,323 B2 | 1/2005 | Yip et al. |
| 6,849,087 B1 | 2/2005 | Chuter |
| 6,863,685 B2 | 3/2005 | Davila et al. |
| 6,866,669 B2 | 3/2005 | Buzzard et al. |
| 6,896,697 B1 | 5/2005 | Yip et al. |
| 6,899,718 B2 | 5/2005 | Gifford, III et al. |
| 6,911,039 B2 | 6/2005 | Shiu et al. |
| 6,913,600 B2 | 7/2005 | Valley et al. |
| 6,942,680 B2 | 9/2005 | Grayzel et al. |
| 6,945,992 B2 | 9/2005 | Goodson, IV et al. |
| 6,951,554 B2 | 10/2005 | Johansen et al. |
| 6,986,784 B1 | 1/2006 | Weiser et al. |
| 7,001,422 B2 | 2/2006 | Escamilla et al. |
| 7,001,424 B2 | 2/2006 | Patel et al. |
| 7,007,698 B2 | 3/2006 | Thornton |
| 7,018,402 B2 | 3/2006 | Vito et al. |
| 7,025,791 B2 | 4/2006 | Levine et al. |
| 7,037,330 B1 | 5/2006 | Rivelli, Jr. et al. |
| 7,041,130 B2 | 5/2006 | Santini, Jr. et al. |
| 7,052,511 B2 | 5/2006 | Weldon |
| 7,087,088 B2 | 8/2006 | Berg et al. |
| 7,105,016 B2 | 9/2006 | Shiu et al. |
| 7,122,043 B2 | 10/2006 | Greenhalgh et al. |
| 7,137,993 B2 | 11/2006 | Acosta et al. |
| 7,147,655 B2 | 12/2006 | Chermoni |
| 7,147,656 B2 | 12/2006 | Andreas et al. |
| 7,147,661 B2 | 12/2006 | Chobotov et al. |
| 7,150,745 B2 | 12/2006 | Stern et al. |
| 7,160,312 B2 | 1/2007 | Saadat |
| 7,163,552 B2 | 1/2007 | Diaz |
| 7,166,125 B1 | 1/2007 | Baker et al. |
| 7,169,158 B2 | 1/2007 | Sniffin et al. |
| 7,169,163 B2 | 1/2007 | Becker |
| 7,172,617 B2 | 2/2007 | Colgan et al. |
| 7,179,284 B2 | 2/2007 | Khosravi et al. |
| 7,186,237 B2 | 3/2007 | Meyer et al. |
| 7,192,440 B2 | 3/2007 | Andreas et al. |
| 7,201,770 B2 | 4/2007 | Johnson et al. |
| 7,211,101 B2 | 5/2007 | Carley et al. |
| 7,243,408 B2 | 7/2007 | Vietmeier |
| 7,258,697 B1 | 8/2007 | Cox et al. |
| 7,261,731 B2 | 8/2007 | Patel et al. |
| 7,267,684 B2 | 9/2007 | Rolando et al. |
| 7,270,673 B2 | 9/2007 | Yee et al. |
| 7,273,492 B2 | 9/2007 | Cheng et al. |
| 7,279,007 B2 | 10/2007 | Nikolic et al. |
| 7,296,577 B2 | 11/2007 | Lashinski et al. |
| 7,300,456 B2 | 11/2007 | Andreas et al. |
| 7,294,146 B2 | 12/2007 | Chew et al. |
| 7,303,572 B2 | 12/2007 | Meisheimer et al. |
| 7,303,580 B2 | 12/2007 | Parker |
| 7,306,617 B2 | 12/2007 | Majercak |
| 7,309,341 B2 | 12/2007 | Ortiz et al. |
| 7,309,350 B2 | 12/2007 | Landreville et al. |
| 7,316,711 B2 | 1/2008 | Allen et al. |
| 7,320,702 B2 | 1/2008 | Hammersmark et al. |
| 7,323,006 B2 | 1/2008 | Andreas et al. |
| 7,323,007 B2 | 1/2008 | Sano |
| 7,326,203 B2 | 2/2008 | Papineau et al. |
| 7,326,236 B2 | 2/2008 | Andreas et al. |
| 7,329,279 B2 | 2/2008 | Haug et al. |
| 7,331,987 B1 | 2/2008 | Cox |
| 7,331,990 B2 | 2/2008 | Gianotti |
| 7,331,992 B2 | 2/2008 | Randall et al. |
| 7,351,255 B2 | 4/2008 | Andreas |
| 7,399,307 B2 | 7/2008 | Evans et al. |
| 7,402,168 B2 | 7/2008 | Sanderson et al. |
| 7,419,501 B2 | 9/2008 | Chiu et al. |
| 7,431,729 B2 | 10/2008 | Chanduszko |
| 7,445,631 B2 | 11/2008 | Salaheih et al. |
| 7,476,245 B2 | 1/2009 | Abbate |
| 7,500,986 B2 | 3/2009 | Lye et al. |
| 7,510,575 B2 | 3/2009 | Spenser et al. |
| 7,524,330 B2 | 4/2009 | Berreklouw |
| 7,537,607 B2 | 5/2009 | Gerberding |
| 7,550,001 B2 | 6/2009 | Dorn et al. |
| 7,578,840 B2 | 8/2009 | Schaeffer |
| 7,604,662 B2 | 10/2009 | Cambronne et al. |
| 7,611,497 B2 | 11/2009 | Wollschlager |
| 7,617,007 B2 | 11/2009 | Williams et al. |

(56) References Cited

U.S. PATENT DOCUMENTS

| | | |
|---|---|---|
| 7,618,432 B2 | 11/2009 | Pedersen et al. |
| 7,618,447 B2 | 11/2009 | Case et al. |
| 7,625,398 B2 | 12/2009 | Clifford et al. |
| 7,628,803 B2 | 12/2009 | Pavcnik et al. |
| 7,655,034 B2 | 2/2010 | Mitchell et al. |
| 7,658,759 B2 | 2/2010 | Case et al. |
| 7,666,216 B2 | 2/2010 | Hogendijk et al. |
| 7,674,282 B2 | 3/2010 | Wu et al. |
| 7,686,824 B2 | 3/2010 | Konstantino et al. |
| 7,695,507 B2 | 4/2010 | Rivelli, Jr. et al. |
| 7,720,521 B2 | 5/2010 | Chang et al. |
| 7,736,387 B2 | 6/2010 | Pollock et al. |
| 7,758,594 B2 | 7/2010 | Lamson et al. |
| 7,758,625 B2 | 7/2010 | Wu et al. |
| 7,758,627 B2 | 7/2010 | Richter |
| 7,758,632 B2 | 7/2010 | Hojeibane et al. |
| 7,763,063 B2 | 7/2010 | Arbefeuille et al. |
| 7,780,716 B2 | 8/2010 | Pappas et al. |
| 7,794,489 B2 | 9/2010 | Shumer et al. |
| 7,799,065 B2 | 9/2010 | Pappas |
| 7,806,918 B2 | 10/2010 | Nissl et al. |
| 7,828,834 B2 | 11/2010 | Garbe |
| 7,833,262 B2 | 11/2010 | McGuckin, Jr. et al. |
| 7,846,194 B2 | 12/2010 | Hartley et al. |
| 7,867,267 B2 | 1/2011 | Sullivan et al. |
| 7,871,431 B2 | 1/2011 | Gurm et al. |
| 7,883,537 B2 | 2/2011 | Grayzel et al. |
| 7,896,911 B2 | 3/2011 | Schneider et al. |
| 7,905,913 B2 | 3/2011 | Chew et al. |
| 7,918,880 B2 | 4/2011 | Austin |
| 7,922,755 B2 | 4/2011 | Acosta et al. |
| 7,933,660 B2 | 4/2011 | Carr |
| 7,938,851 B2 | 5/2011 | Olson et al. |
| 7,955,315 B2 | 6/2011 | Feinberg et al. |
| 7,963,987 B2 | 6/2011 | Melsheimer et al. |
| 7,967,855 B2 | 6/2011 | Furst et al. |
| 7,972,373 B2 | 7/2011 | Contiliano et al. |
| 8,002,725 B2 | 8/2011 | Hogendijk |
| 8,024,851 B2 | 9/2011 | Barr et al. |
| 8,034,099 B2 | 10/2011 | Pellegrini |
| 8,043,354 B2 | 10/2011 | Greenberg et al. |
| 8,043,357 B2 | 10/2011 | Hartley |
| 8,048,151 B2 | 11/2011 | O'Brien et al. |
| 8,052,738 B2 | 11/2011 | Craven |
| 8,057,543 B2 | 11/2011 | O'Brien et al. |
| 8,062,344 B2 | 11/2011 | Dorn et al. |
| 8,075,607 B2 | 12/2011 | Melsheimer et al. |
| 8,092,468 B2 | 1/2012 | Hansen |
| 8,100,958 B2 | 1/2012 | Fischer et al. |
| 8,128,677 B2 | 3/2012 | Schneider et al. |
| 8,157,851 B2 | 4/2012 | Andreas |
| 8,177,831 B2 | 5/2012 | Andreas |
| 8,236,045 B2 | 8/2012 | Benichou et al. |
| 8,292,938 B2 | 10/2012 | Case |
| 8,308,790 B2 | 11/2012 | Arbefeuille et al. |
| 8,317,859 B2 | 11/2012 | Snow et al. |
| 8,323,243 B2 | 12/2012 | Schneider et al. |
| 8,328,864 B2 | 12/2012 | Niermann |
| 8,353,945 B2 | 1/2013 | Andreas et al. |
| 8,366,766 B2 | 2/2013 | Berreklouw |
| 8,382,813 B2 | 2/2013 | Shumer |
| 8,394,139 B2 | 3/2013 | Roeder et al. |
| 8,403,978 B2 | 3/2013 | Schlun et al. |
| 8,409,267 B2 | 4/2013 | Berez et al. |
| 8,414,636 B2 | 4/2013 | Nabulsi et al. |
| 8,460,357 B2 | 6/2013 | McGarry et al. |
| 8,460,368 B2 | 6/2013 | Taylor et al. |
| 8,474,460 B2 | 7/2013 | Barrett et al. |
| 8,486,128 B2 | 7/2013 | Jen et al. |
| 8,500,787 B2 | 8/2013 | Simpson et al. |
| 8,500,789 B2 | 8/2013 | Wuebbeling et al. |
| 8,540,760 B2 | 9/2013 | Paul, Jr. et al. |
| 8,585,747 B2 | 11/2013 | Andreas et al. |
| 8,740,973 B2 | 6/2014 | Furst et al. |
| 8,771,335 B2 | 7/2014 | Griego et al. |
| 8,784,467 B2 | 7/2014 | Connelly et al. |
| 8,784,468 B2 | 7/2014 | Gerdts et al. |
| 8,821,563 B2 | 9/2014 | Orr et al. |
| 8,864,811 B2 | 10/2014 | Kao |
| 8,888,834 B2 | 11/2014 | Hansen et al. |
| 8,888,841 B2 | 11/2014 | Pandelidis et al. |
| 8,900,289 B2 | 12/2014 | Thompson |
| 8,911,487 B2 | 12/2014 | Bennett et al. |
| 8,956,398 B2 | 2/2015 | George et al. |
| 8,961,583 B2 | 2/2015 | Hojeibane et al. |
| 8,968,383 B1 | 3/2015 | Johnson et al. |
| 8,986,362 B2 | 3/2015 | Snow et al. |
| 9,023,095 B2 | 5/2015 | Bueche et al. |
| 9,050,181 B2 | 6/2015 | Hartley |
| 9,101,503 B2 | 8/2015 | Lowe et al. |
| 9,101,506 B2 | 8/2015 | Arbefeuille et al. |
| 9,113,999 B2 | 8/2015 | Taylor et al. |
| 9,149,379 B2 | 10/2015 | Keady et al. |
| 9,192,500 B1 | 11/2015 | Longo et al. |
| 9,198,783 B2 | 12/2015 | Douk et al. |
| 9,216,082 B2 | 12/2015 | Von Segesser et al. |
| 9,237,959 B2 | 1/2016 | Cage |
| 9,301,864 B2 | 4/2016 | Kao |
| 9,314,360 B2 | 4/2016 | Kao |
| 9,370,437 B2 | 6/2016 | Chuter et al. |
| 9,375,327 B2 | 6/2016 | Giasolli et al. |
| 9,375,336 B1 | 6/2016 | Longo et al. |
| 9,398,967 B2 | 7/2016 | Cornelius |
| 9,421,115 B2 | 8/2016 | Wübbeling et al. |
| 9,433,520 B2 * | 9/2016 | Longo .................. A61F 2/844 |
| 9,539,130 B2 | 1/2017 | Farag et al. |
| 9,566,179 B2 | 2/2017 | Andreas et al. |
| 9,597,213 B2 | 3/2017 | Green |
| 9,724,224 B2 | 8/2017 | Gillick et al. |
| 9,730,818 B2 | 8/2017 | Giasolli et al. |
| 9,867,699 B2 | 1/2018 | Straubinger et al. |
| 9,877,828 B2 | 1/2018 | Straubinger et al. |
| 9,918,835 B2 | 3/2018 | Guyenot et al. |
| 2001/0039446 A1 | 11/2001 | Edwin et al. |
| 2002/0120323 A1 | 8/2002 | Thompson |
| 2002/0123790 A1 | 9/2002 | White et al. |
| 2002/0151955 A1 * | 10/2002 | Tran .................. A61F 2/95 623/1.12 |
| 2002/0169495 A1 | 11/2002 | Gifford et al. |
| 2003/0055480 A1 * | 3/2003 | Fischell .................. A61F 2/013 623/1.11 |
| 2003/0055491 A1 | 3/2003 | Schwartz et al. |
| 2003/0069630 A1 | 4/2003 | Burgermeister et al. |
| 2003/0074049 A1 | 4/2003 | Hoganson et al. |
| 2003/0130720 A1 | 7/2003 | DePalma et al. |
| 2003/0220683 A1 | 11/2003 | Minasian et al. |
| 2003/0225446 A1 | 12/2003 | Hartley |
| 2003/0225448 A1 | 12/2003 | Gerberding |
| 2004/0010307 A1 | 1/2004 | Grad et al. |
| 2004/0186551 A1 | 9/2004 | Kao et al. |
| 2004/0215324 A1 | 10/2004 | Vonderwalde et al. |
| 2004/0267348 A1 | 12/2004 | Gunderson et al. |
| 2005/0010275 A1 | 1/2005 | Sahatjian |
| 2005/0021123 A1 | 1/2005 | Dorn et al. |
| 2005/0096731 A1 | 5/2005 | Looi et al. |
| 2005/0149163 A1 | 7/2005 | Sahota |
| 2005/0246008 A1 | 11/2005 | Hogendijk et al. |
| 2005/0251164 A1 | 11/2005 | Gifford, III et al. |
| 2005/0273151 A1 | 12/2005 | Fulkerson |
| 2005/0278011 A1 * | 12/2005 | Peckham .................. A61F 2/958 623/1.11 |
| 2005/0288763 A1 * | 12/2005 | Andreas .................. A61F 2/95 623/1.11 |
| 2005/0288764 A1 | 12/2005 | Snow et al. |
| 2005/0288766 A1 | 12/2005 | Plain et al. |
| 2006/0069424 A1 | 3/2006 | Acosta et al. |
| 2006/0074478 A1 | 4/2006 | Feller, III |
| 2006/0111769 A1 | 5/2006 | Murray |
| 2006/0184225 A1 | 8/2006 | Pryor |
| 2006/0184226 A1 * | 8/2006 | Austin .................. A61F 2/95 623/1.11 |
| 2006/0184227 A1 | 8/2006 | Rust |
| 2006/0206190 A1 | 9/2006 | Chermoni |
| 2006/0248698 A1 | 11/2006 | Hanson et al. |

(56) References Cited

U.S. PATENT DOCUMENTS

| | | |
|---|---|---|
| 2006/0282149 A1 | 12/2006 | Kao |
| 2006/0282150 A1* | 12/2006 | Olson ............... A61F 2/966 623/1.11 |
| 2007/0088420 A1 | 4/2007 | Andreas et al. |
| 2007/0093744 A1 | 4/2007 | Elmaleh |
| 2007/0142892 A1 | 6/2007 | Dave et al. |
| 2007/0156223 A1 | 7/2007 | Vaughan |
| 2007/0156224 A1 | 7/2007 | Cioanta et al. |
| 2007/0156225 A1 | 7/2007 | George et al. |
| 2007/0179587 A1 | 8/2007 | Acosta et al. |
| 2007/0191926 A1 | 8/2007 | Nikanorov et al. |
| 2007/0233235 A1 | 10/2007 | Chouinard |
| 2008/0033522 A1 | 2/2008 | Grewe et al. |
| 2008/0051867 A1 | 2/2008 | Davila et al. |
| 2008/0077229 A1 | 3/2008 | Andreas et al. |
| 2008/0082154 A1 | 4/2008 | Tseng et al. |
| 2008/0132999 A1 | 6/2008 | Mericle et al. |
| 2008/0208327 A1 | 8/2008 | Rowe |
| 2008/0221658 A1 | 9/2008 | Martin et al. |
| 2008/0234795 A1 | 9/2008 | Snow et al. |
| 2008/0255653 A1 | 10/2008 | Schkolnik |
| 2008/0264102 A1 | 10/2008 | Berra |
| 2008/0319528 A1 | 12/2008 | Yribarren et al. |
| 2009/0048654 A1 | 2/2009 | Chmura et al. |
| 2009/0069878 A1 | 3/2009 | Weber et al. |
| 2009/0076594 A1 | 3/2009 | Sabaria |
| 2009/0082841 A1 | 3/2009 | Zacharias et al. |
| 2009/0099641 A1 | 4/2009 | Wu et al. |
| 2009/0149943 A1 | 6/2009 | Tower |
| 2009/0214615 A1 | 8/2009 | Zhao |
| 2009/0216284 A1 | 8/2009 | Chin et al. |
| 2009/0248141 A1 | 10/2009 | Shandas et al. |
| 2009/0270965 A1 | 10/2009 | Sinha et al. |
| 2009/0270967 A1 | 10/2009 | Fleming, III et al. |
| 2009/0276031 A1 | 11/2009 | Kao |
| 2010/0042121 A1 | 2/2010 | Schneider et al. |
| 2010/0131045 A1 | 5/2010 | Globerman et al. |
| 2010/0137966 A1 | 6/2010 | Magnuson |
| 2010/0145431 A1 | 6/2010 | Wu et al. |
| 2010/0228333 A1 | 9/2010 | Drasler et al. |
| 2010/0318173 A1 | 12/2010 | Kolandaivelu et al. |
| 2011/0004237 A1 | 1/2011 | Schneider et al. |
| 2011/0077731 A1 | 3/2011 | Lee et al. |
| 2011/0082490 A1 | 4/2011 | Connelly et al. |
| 2011/0125248 A1 | 5/2011 | George et al. |
| 2011/0152992 A1 | 6/2011 | Schneider et al. |
| 2011/0190864 A1 | 8/2011 | McClain et al. |
| 2011/0230954 A1 | 9/2011 | Schneider et al. |
| 2012/0016457 A1 | 1/2012 | Chobotov et al. |
| 2012/0035705 A1 | 2/2012 | Giasolli et al. |
| 2012/0041469 A1 | 2/2012 | Fischell et al. |
| 2012/0083872 A1 | 4/2012 | Schneider et al. |
| 2012/0172963 A1 | 7/2012 | Ryan et al. |
| 2012/0191176 A1 | 7/2012 | Nagl et al. |
| 2012/0226343 A1 | 9/2012 | Vo et al. |
| 2013/0138202 A1* | 5/2013 | Paul ............... A61F 2/82 623/1.15 |
| 2013/0144375 A1 | 6/2013 | Giasolli et al. |
| 2014/0081380 A1 | 3/2014 | Giasolli et al. |
| 2014/0094929 A1 | 4/2014 | Shin et al. |
| 2014/0135897 A1 | 5/2014 | Cully et al. |
| 2014/0194967 A1 | 7/2014 | Schneider et al. |
| 2014/0200648 A1 | 7/2014 | Newell et al. |
| 2014/0214068 A1* | 7/2014 | Zhu ............... A61M 25/1029 606/194 |
| 2014/0288629 A1 | 9/2014 | Amendt |
| 2015/0297378 A1 | 10/2015 | Senness et al. |
| 2016/0220401 A1 | 8/2016 | Longo et al. |
| 2016/0374839 A1 | 12/2016 | Longo et al. |
| 2017/0000629 A1 | 1/2017 | Giasolli et al. |
| 2017/0181873 A1 | 6/2017 | Schneider et al. |
| 2017/0296366 A1 | 10/2017 | Giasolli et al. |
| 2017/0319361 A1 | 11/2017 | Giasolli et al. |
| 2017/0319364 A1 | 11/2017 | Jung et al. |
| 2018/0000619 A1 | 1/2018 | Longo et al. |
| 2018/0110634 A1 | 4/2018 | Giasolli et al. |
| 2018/0200085 A1 | 7/2018 | Giasolli et al. |
| 2018/0200086 A1 | 7/2018 | Giasolli et al. |
| 2018/0200087 A1 | 7/2018 | Giasolli et al. |
| 2018/0207007 A1 | 7/2018 | Giasolli et al. |
| 2018/0207008 A1 | 7/2018 | Giasolli et al. |

FOREIGN PATENT DOCUMENTS

| | | |
|---|---|---|
| AU | 2014201067 | 3/2014 |
| AU | 2010259907 | 8/2015 |
| AU | 2013212056 | 7/2016 |
| AU | 2015207895 | 5/2017 |
| AU | 2014280976 | 7/2017 |
| CA | 2705275 | 7/2013 |
| CN | 101262835 | 9/2008 |
| CN | 101754727 | 6/2010 |
| CN | 102724931 | 10/2012 |
| CN | 103313682 | 9/2013 |
| CN | 104220026 | 12/2014 |
| CN | 104887365 | 9/2015 |
| CN | 103313682 | 8/2016 |
| CN | 104220026 | 9/2016 |
| CN | 106466205 | 3/2017 |
| CN | 106473786 | 3/2017 |
| CN | 106473849 | 3/2017 |
| CN | 107028691 | 8/2017 |
| CN | 107157632 | 9/2017 |
| CN | 107205834 | 9/2017 |
| CN | 107405208 | 11/2017 |
| CN | 104887365 | 12/2017 |
| CN | 107427375 | 12/2017 |
| DE | 60030705 | 5/2007 |
| DE | 10 2009 041 025 | 3/2011 |
| DE | 20 2011 107 781 | 12/2011 |
| DE | 20 2011 110 714 | 12/2015 |
| DE | 10 2014 016 588 | 5/2016 |
| DE | 20 2011 110 818 | 9/2016 |
| DK | 2775968 | 12/2017 |
| EP | 0497620 | 8/1992 |
| EP | 0714640 | 6/1996 |
| EP | 0855883 | 8/1998 |
| EP | 0812580 | 2/2004 |
| EP | 1393766 | 3/2004 |
| EP | 1787593 | 5/2007 |
| EP | 1803423 | 7/2007 |
| EP | 1894545 | 3/2008 |
| EP | 2219535 | 8/2010 |
| EP | 2440155 | 4/2012 |
| EP | 2806826 | 12/2014 |
| EP | 2881086 | 6/2015 |
| EP | 2699207 | 10/2015 |
| EP | 2590602 | 12/2015 |
| EP | 3015078 | 5/2016 |
| EP | 3058900 | 8/2016 |
| EP | 3072463 | 9/2016 |
| EP | 2775968 | 9/2017 |
| EP | 3217927 | 9/2017 |
| EP | 3250159 | 12/2017 |
| FR | 2714816 | 7/1995 |
| GB | 201106757 | 6/2011 |
| JP | H11-501526 | 2/1999 |
| JP | H11-506665 | 6/1999 |
| JP | 2002-513298 | 5/2002 |
| JP | 2007-503923 | 3/2007 |
| JP | 2007-504897 | 3/2007 |
| JP | 2007-508112 | 4/2007 |
| JP | 2008-504078 | 2/2008 |
| JP | 2008-507376 | 3/2008 |
| JP | 2008-510587 | 4/2008 |
| JP | 2008-246214 | 10/2008 |
| JP | 2008-537891 | 10/2008 |
| JP | 2012-523922 | 10/2012 |
| JP | 2015-506760 | 3/2015 |
| JP | 2016-135278 | 7/2016 |
| JP | 2016-147051 | 8/2016 |
| JP | 6006808 | 10/2016 |
| KR | 10-2017-0084214 | 7/2017 |
| WO | WO 1996/009013 | 3/1996 |

(56) References Cited

FOREIGN PATENT DOCUMENTS

| | | |
|---|---|---|
| WO | WO 1996/037167 | 11/1996 |
| WO | WO 1998/007390 | 2/1998 |
| WO | WO 1999/048440 | 9/1999 |
| WO | WO 1999/049440 | 9/1999 |
| WO | WO 2000/066034 | 11/2000 |
| WO | WO 2001/076509 | 10/2001 |
| WO | WO 2003/047651 | 6/2003 |
| WO | WO 2003/101310 | 12/2003 |
| WO | WO 2004/006983 | 1/2004 |
| WO | WO 2004/032799 | 4/2004 |
| WO | WO 2005/039449 | 5/2005 |
| WO | WO 2006/014767 | 2/2006 |
| WO | WO 2006/026371 | 3/2006 |
| WO | WO 2006/026377 | 3/2006 |
| WO | WO 2006/110258 | 10/2006 |
| WO | WO 2007/088549 | 8/2007 |
| WO | WO 2007/109621 | 9/2007 |
| WO | WO 2009/076517 | 6/2009 |
| WO | WO 2010/037141 | 4/2010 |
| WO | WO 2010/044874 | 4/2010 |
| WO | WO 2010/118432 | 10/2010 |
| WO | WO 2010/144845 | 12/2010 |
| WO | WO 2011/153110 | 12/2011 |
| WO | WO 2012/006602 | 1/2012 |
| WO | WO 2012/143731 | 10/2012 |
| WO | WO 2013/068127 | 5/2013 |
| WO | WO 2013/112768 | 8/2013 |
| WO | WO 2013/118362 | 8/2013 |
| WO | WO 2004/091441 | 10/2014 |
| WO | WO 2016/074799 | 5/2016 |
| WO | WO 2016/122947 | 8/2016 |
| WO | WO 2017/117391 | 7/2017 |

OTHER PUBLICATIONS

English translation of the first Office Action and Search Report in Chinese Application No. 201610546643.5 in 5 pages dated Oct. 17, 2017.

Bosiers, M. et al., "Results from the Tack Optimized Balloon Angioplasty (TOBA) study demonstrate the benefits of minimal metal implants for dissection repair after angioplasty", Journal of Vascular Surgery, vol. 64, Jul. 2016, in 8 pages.

Kokkinidis, D. et al., "Emerging and Future Therapeutic Options for Femoropopliteal and Infrapopliteal Endovascular Intervention", Interventional Cardiology Clinics, vol. 6, 2017, in 17 pages.

Shishehbor, M. et al., "Endovascular Treatment of Femoropopliteal Lesions", Journal of the American College of Cardiology, vol. 66, 2015, in 4 pages.

Zeller, T. et al., "Novel Approaches to the Management of Advanced Peripheral Artery Disease: Perspectives on Drug-Coated Balloons, Drug-Eluting Stents, and Bioresorbable Scaffolds", Current Cardiology Reports, vol. 17, Sep. 2015, in 6 pages.

International Preliminary Report on Patentability, re PCT Application No. PCT/US2008/086396, dated Jun. 15, 2010.

International Preliminary Report on Patentability, re PCT Application No. PCT/US2011/038468, dated Dec. 13, 2012.

International Preliminary Report on Patentability, re PCT Application No. PCT/US2011/043471, dated Jan. 17, 2013.

International Preliminary Report on Patentability, re PCT Application No. PCT/US2013/023030, dated Aug. 7, 2014.

Japanese Office Action, re JP Application No. 2016-014565, dated Feb. 3, 2017.

PCT Search Report and Written Opinion in PCT App. PCT/US2016/069211 dated Mar. 27, 2017 in 19 pages.

Colombo et al., "Intravascular Ultrasound-Guided Percutaneous Transluminal Coronary Angioplast With Provisional Spot Stenting for Treatment of Long Coronary Lesions", Journal of the American College of Cardiology, vol. 38, No. 5, Nov. 1, 2001.

Mosseri et al., "New Indicator for Stent Covering Area", in Catheterization and Cardiovascular Diagnosis, 1998, vol. 44, pp. 188-192.

Australian Office Action (Notice of Acceptance), re AU Application No. 2011274392, dated Nov. 14, 2013, including accepted (allowed) claims.

Australian Office Action, re AU Application No. 2008335140, dated Apr. 21, 2011.

Australian Office Action, re AU Application No. 2008335140, dated Mar. 15, 2011.

Australian Office Action, re AU Application No. 2011274392, dated May 3, 2013.

European Office Action and Supplemental European Search Report, re EP Application No. 11804455.1, dated Jun. 11, 2014.

European Office Action and Supplementary Partial European Search Report, re EP Application No. 08858824.9, dated Sep. 27, 2012.

International Search Report and Written Opinion, re PCT Application No. PCT/US2010/038379, dated Feb. 25, 2011.

International Search Report and Written Opinion, re PCT Application No. PCT/US2011/038468, dated Jan. 18, 2012.

International Search Report and Written Opinion, re PCT Application No. PCT/US2013/023030, dated Apr. 16, 2013.

International Search Report and Written Opinion, re PCT Application No. PCT/US2016/014161, dated Apr. 12, 2016.

International Search Report and Written Opinion, re PCT Application PCT/US2008/086396, dated Jul. 27, 2009.

International Search Report and Written Opinion, re PCT Application PCT/US2011/043471, dated Feb. 9, 2012.

International Search Report, re PCT Application No. PCT/US2013/023030, dated Apr. 16, 2013.

\* cited by examiner

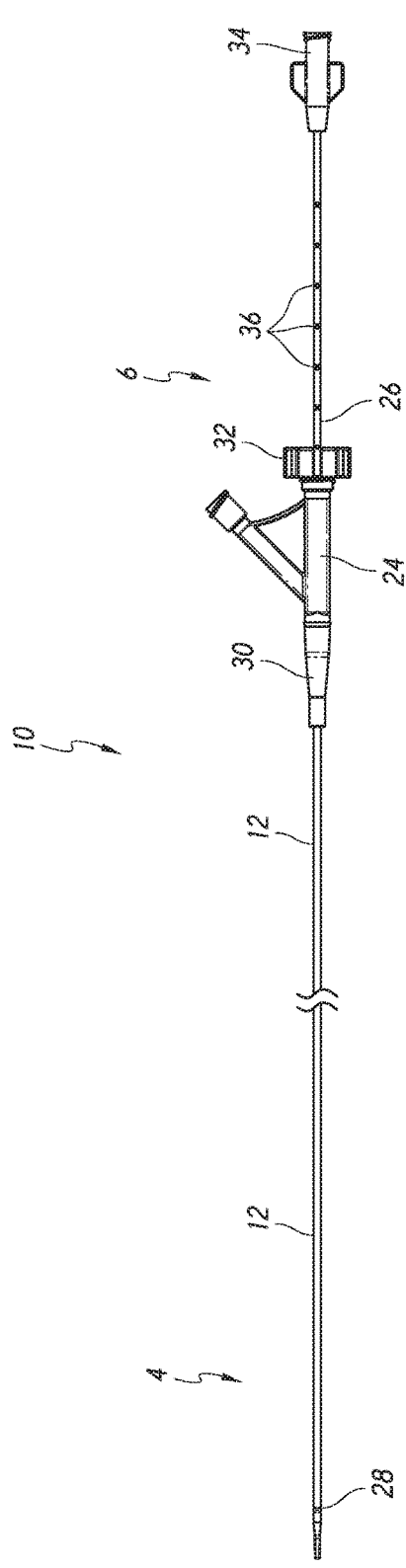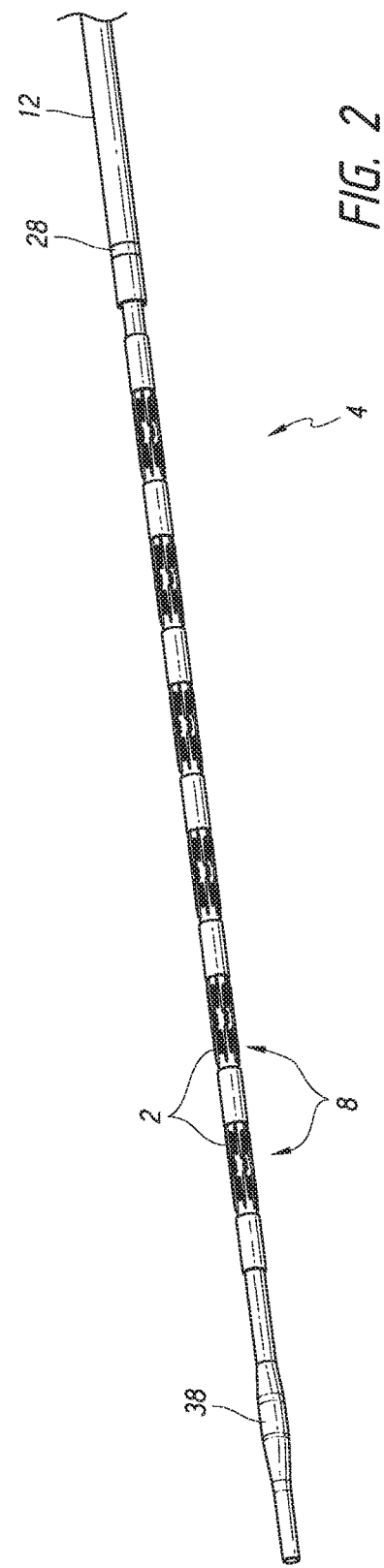

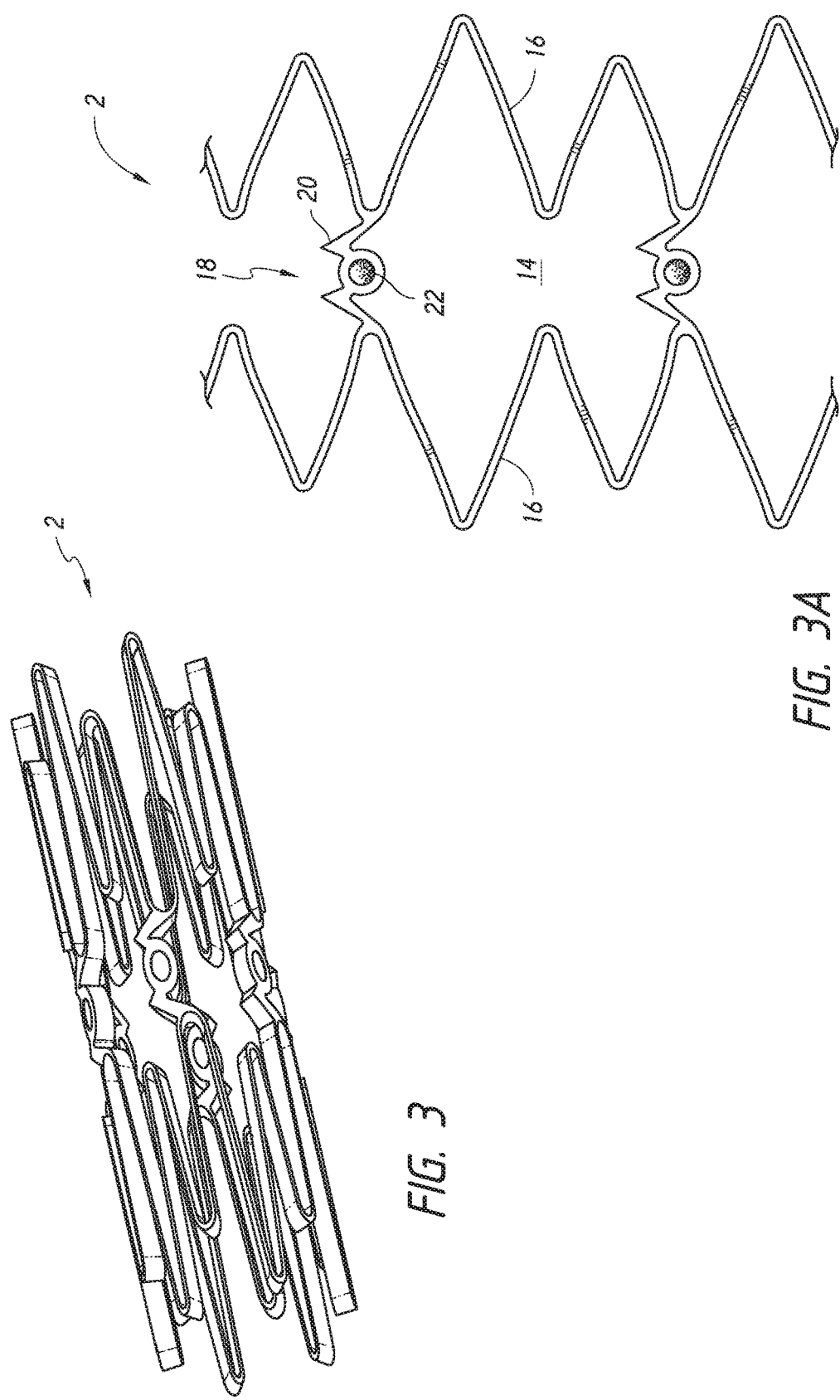

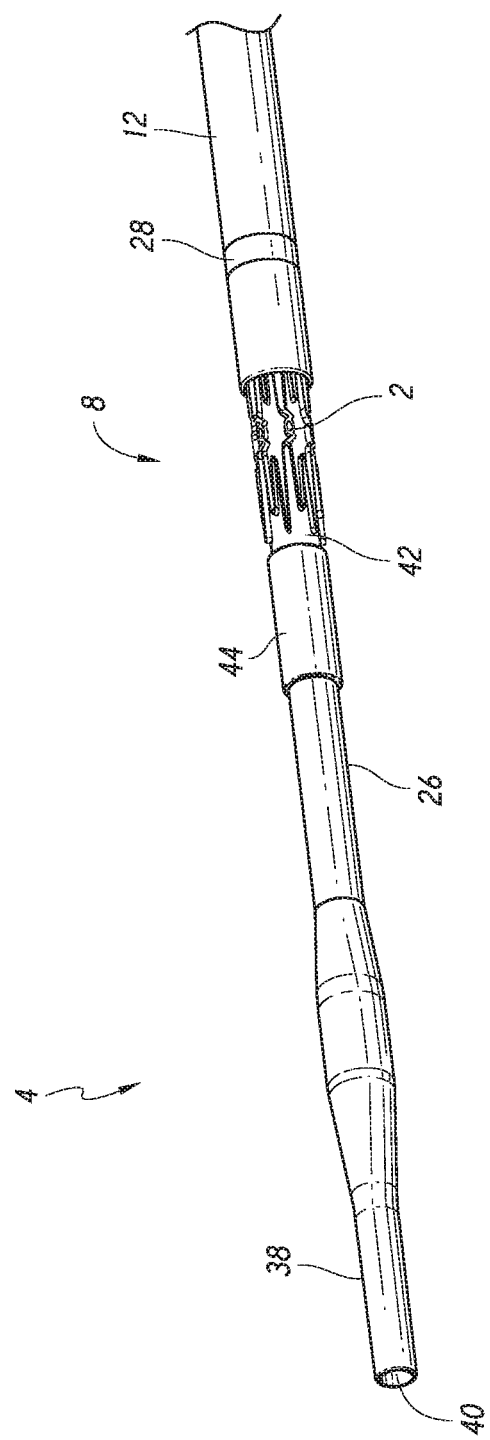

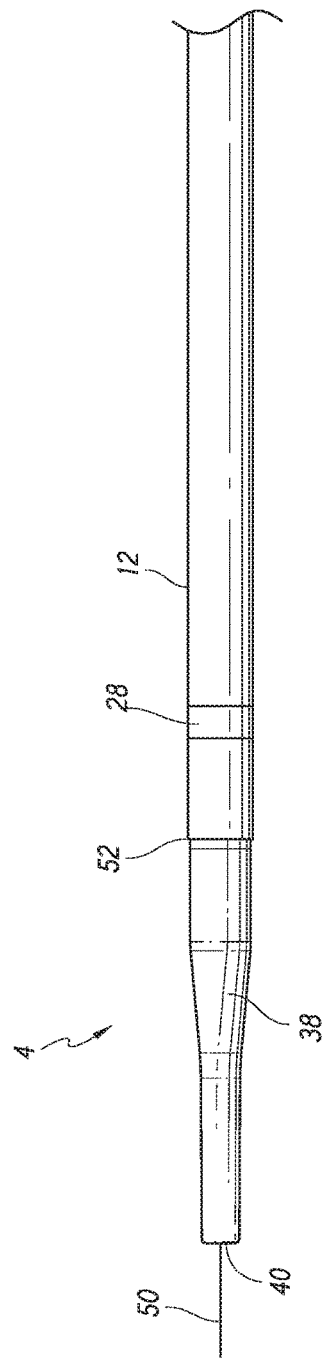
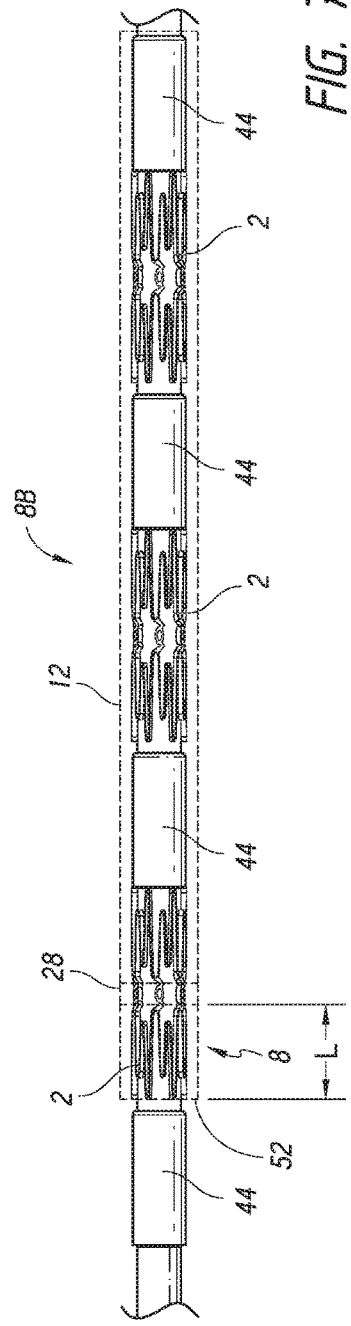
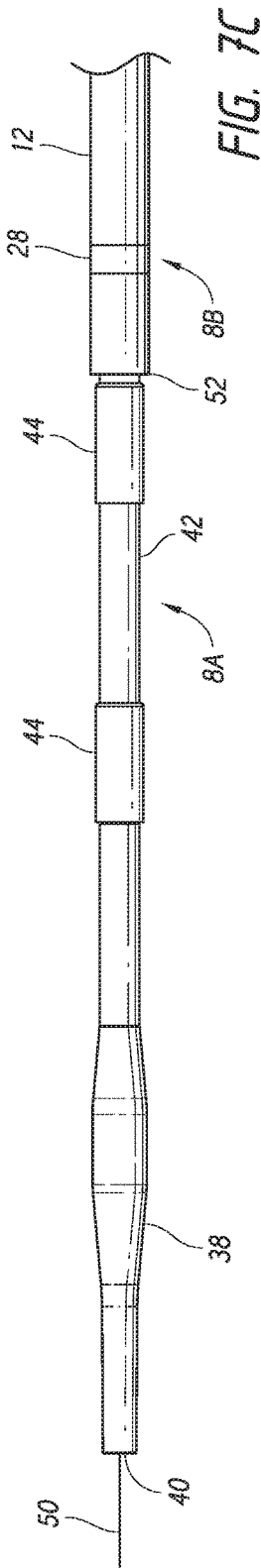
FIG. 7A
FIG. 7B
FIG. 7C

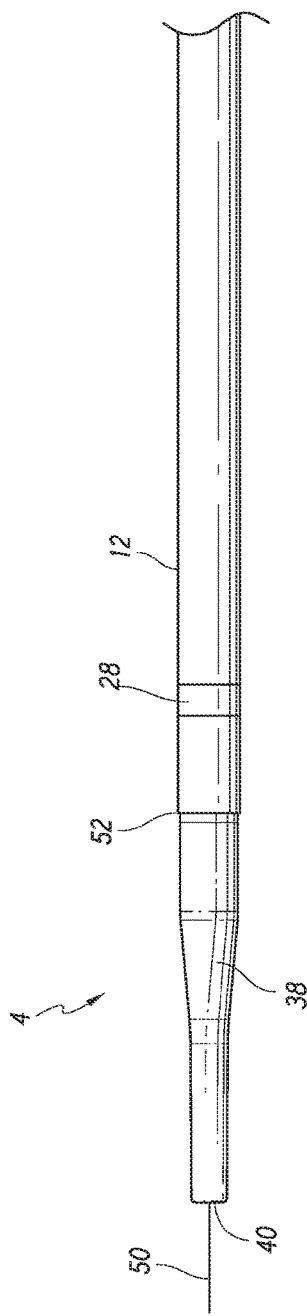
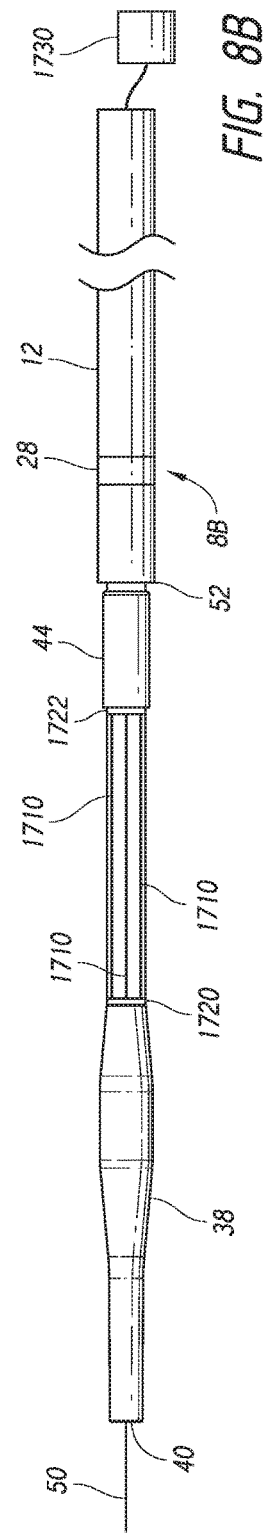
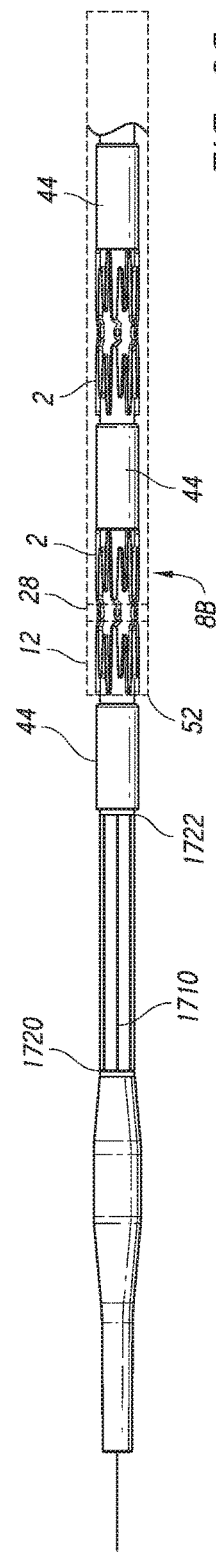

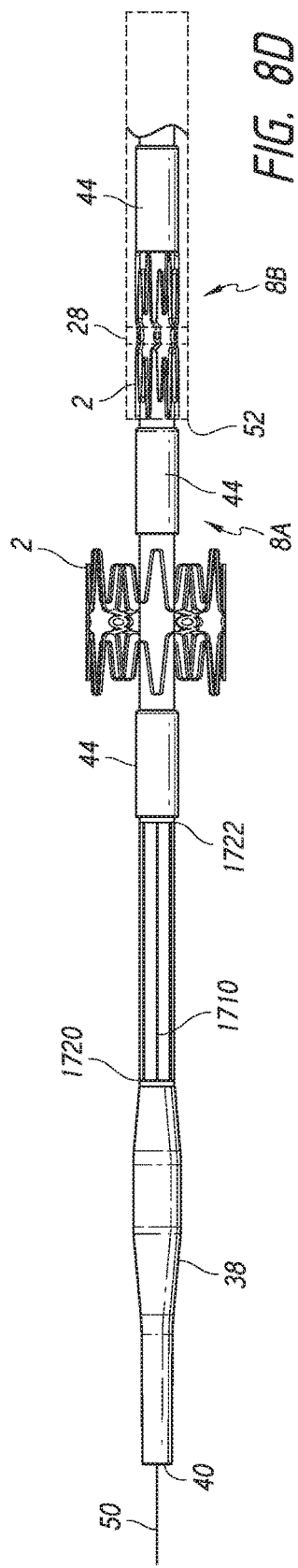
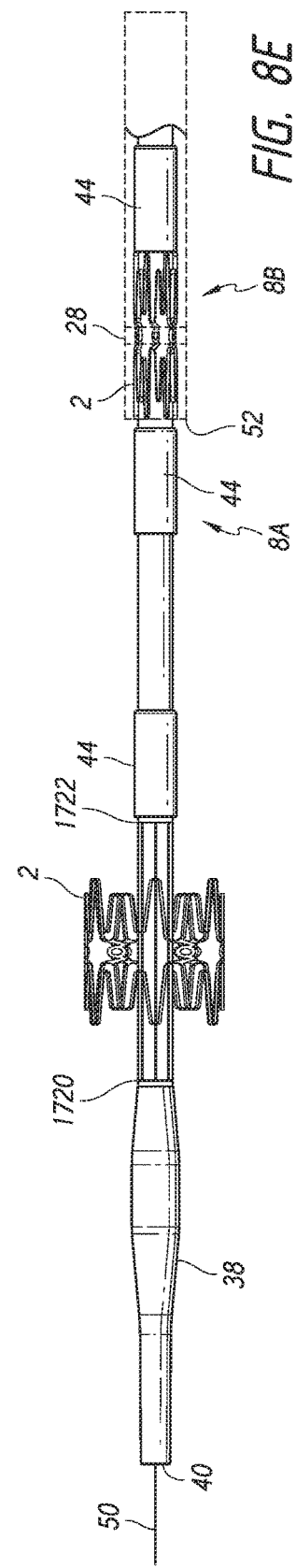
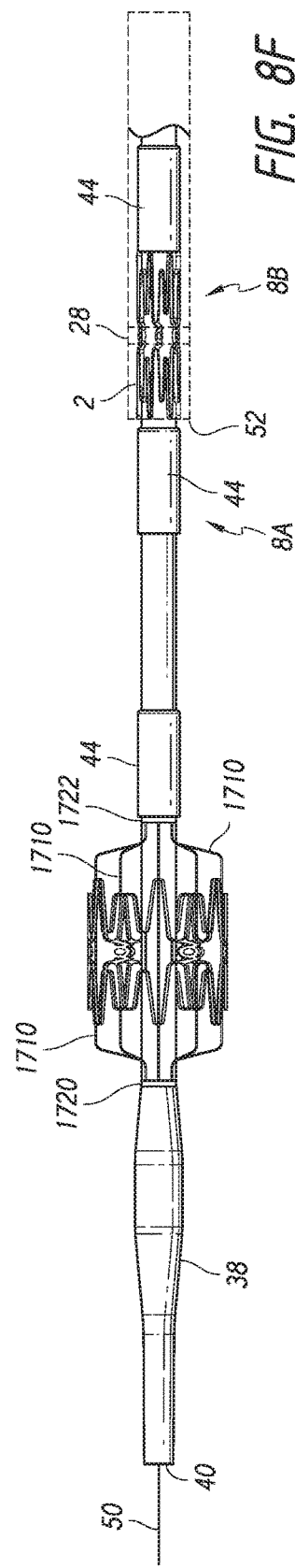
FIG. 8D
FIG. 8E
FIG. 8F

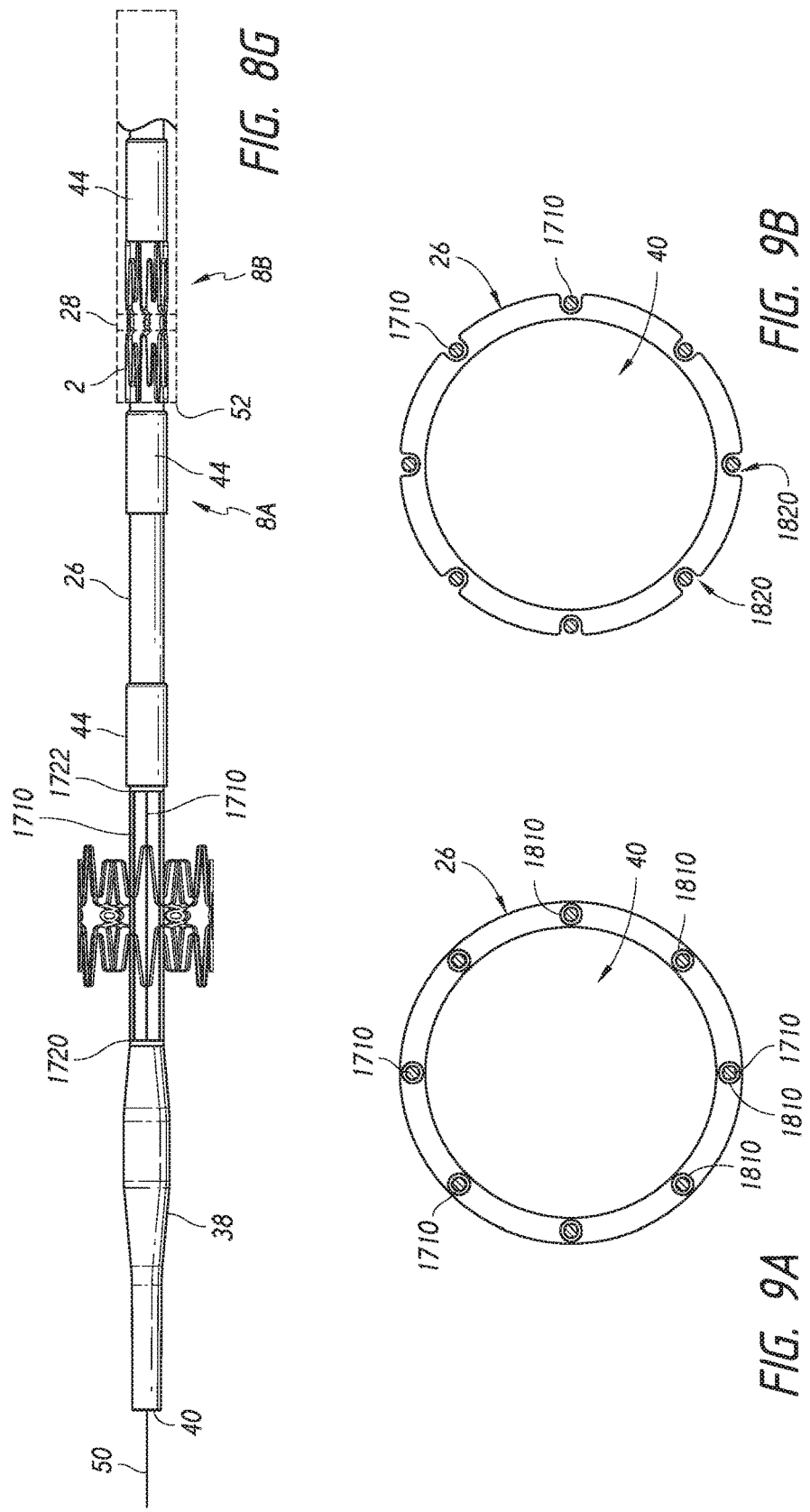

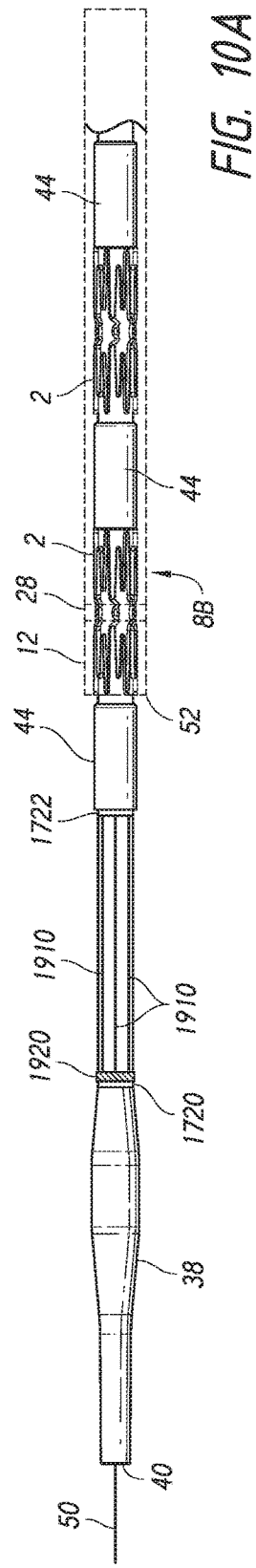
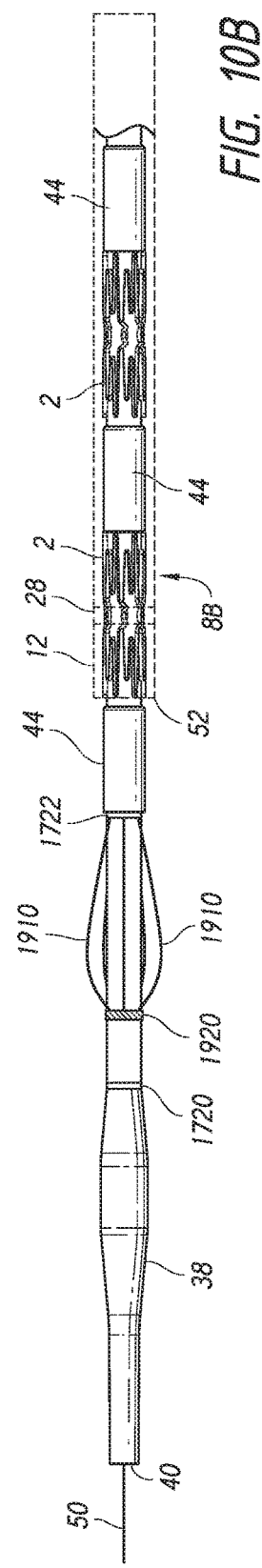
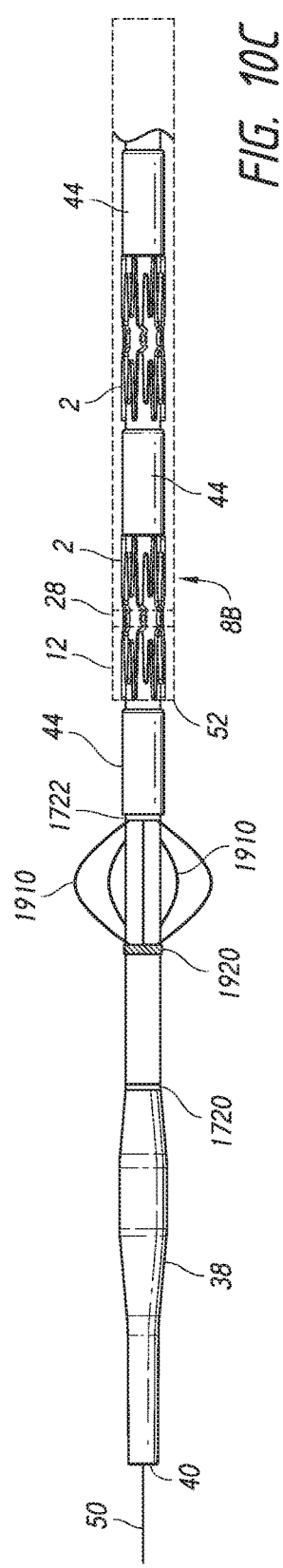

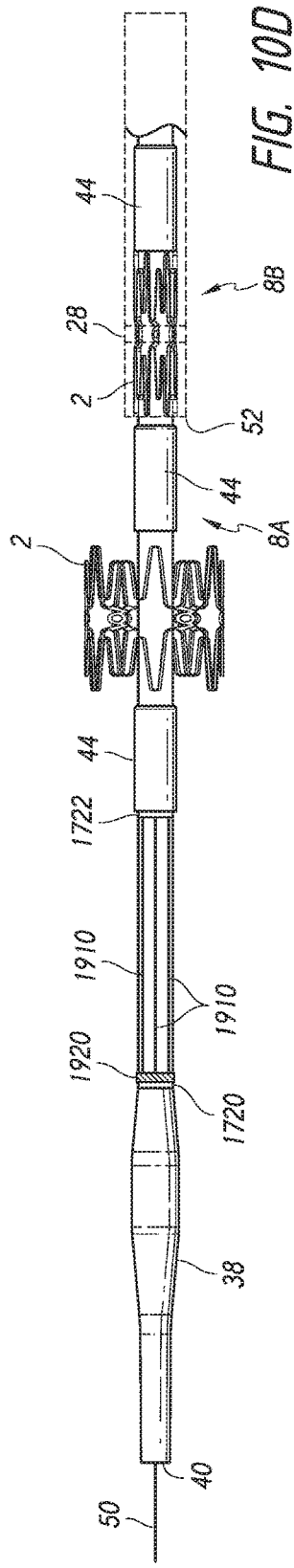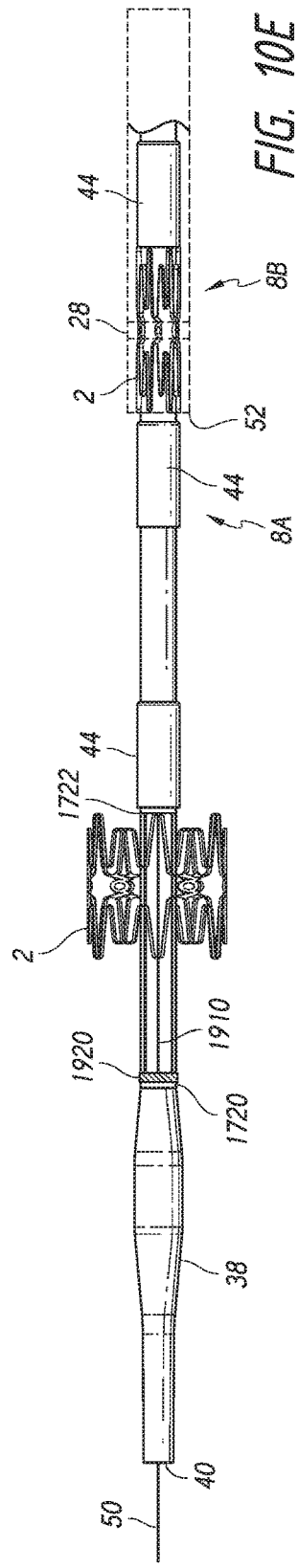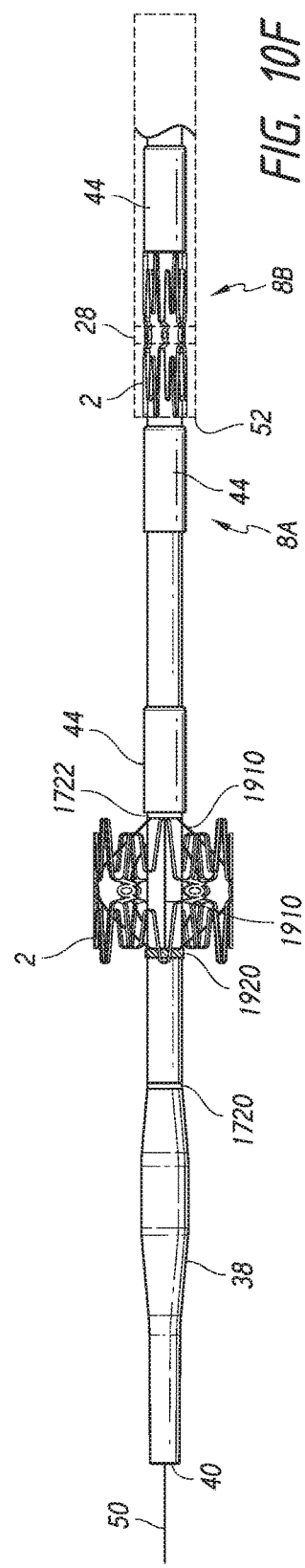

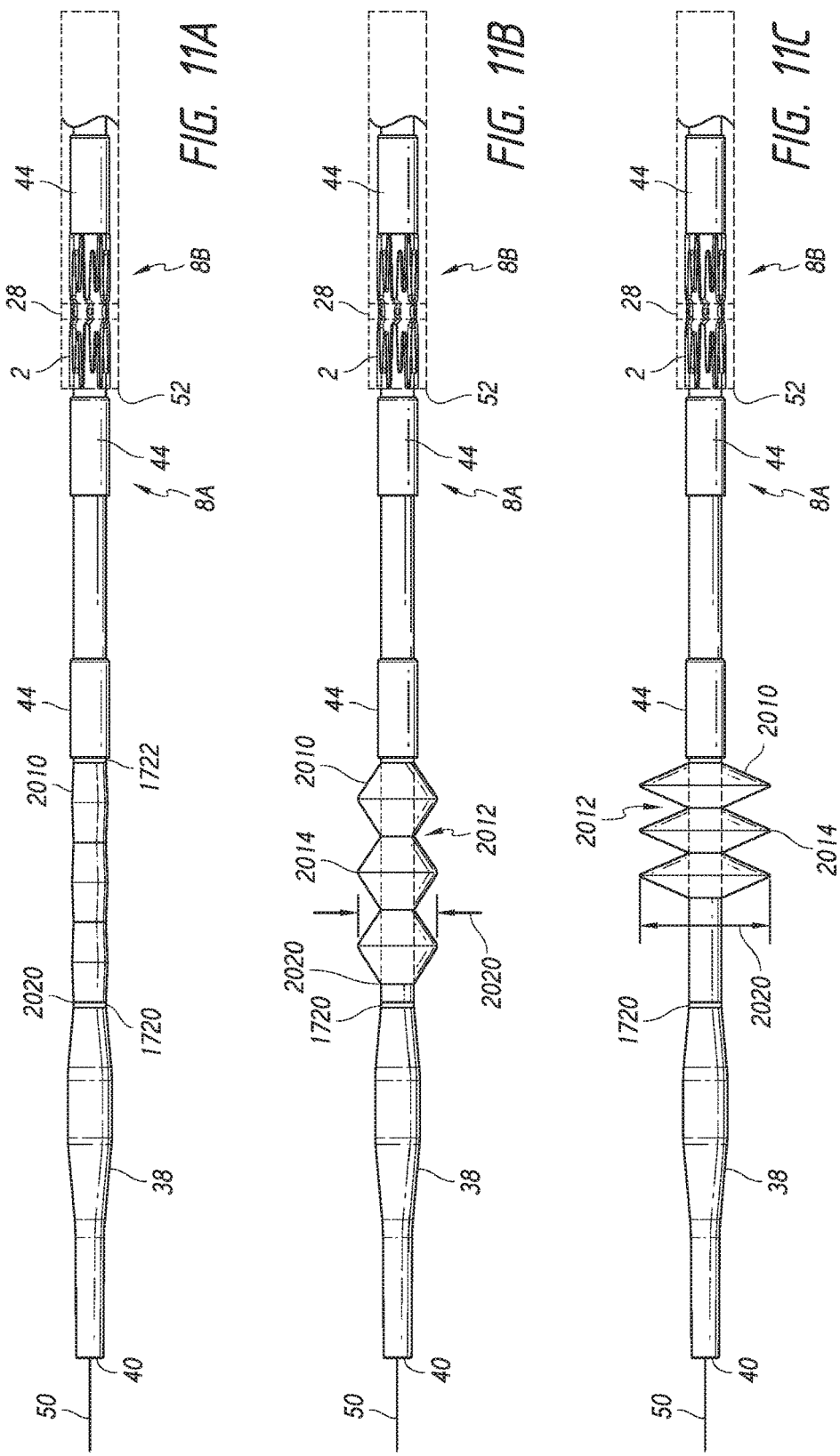

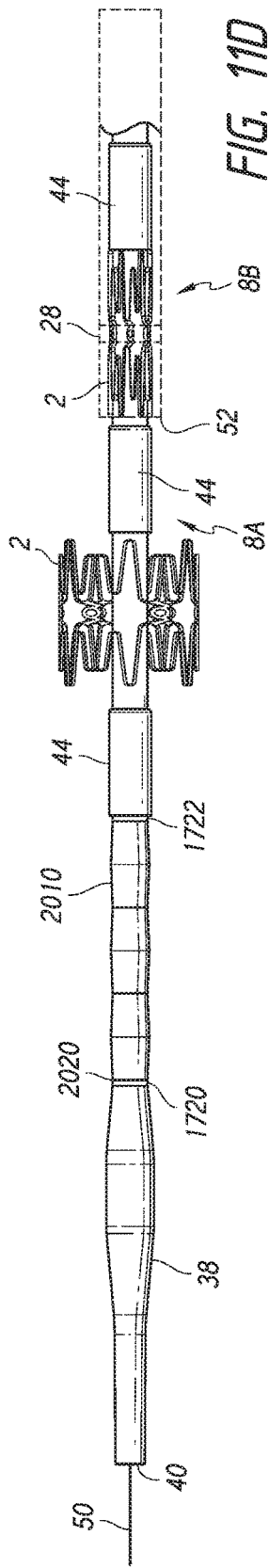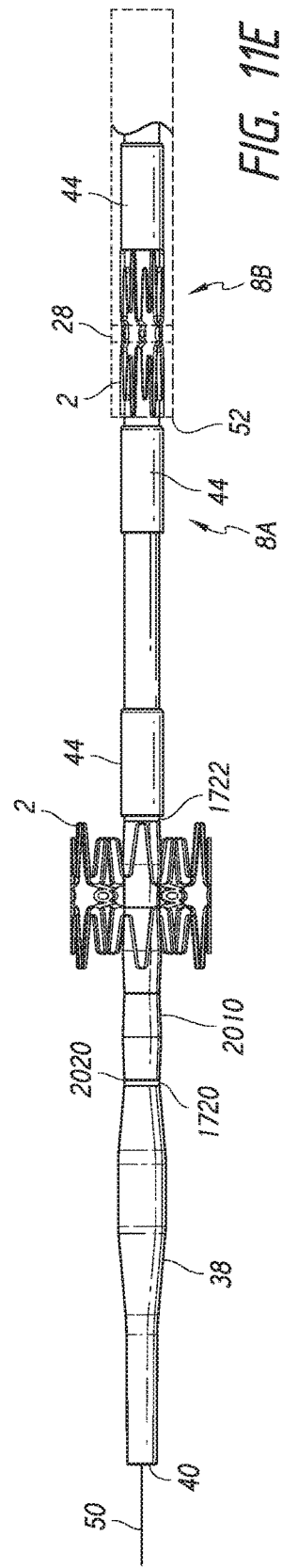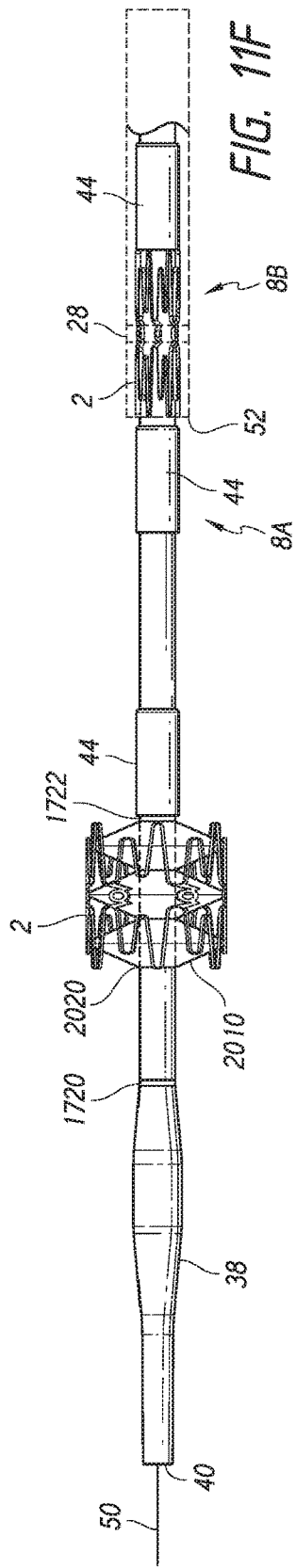

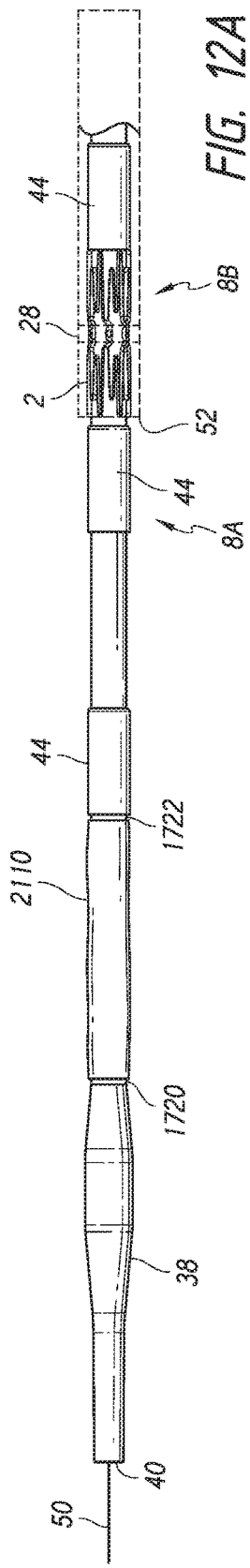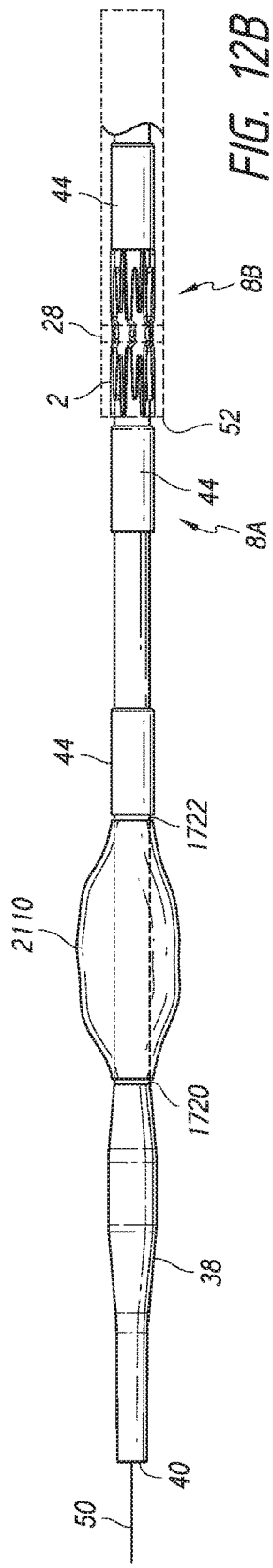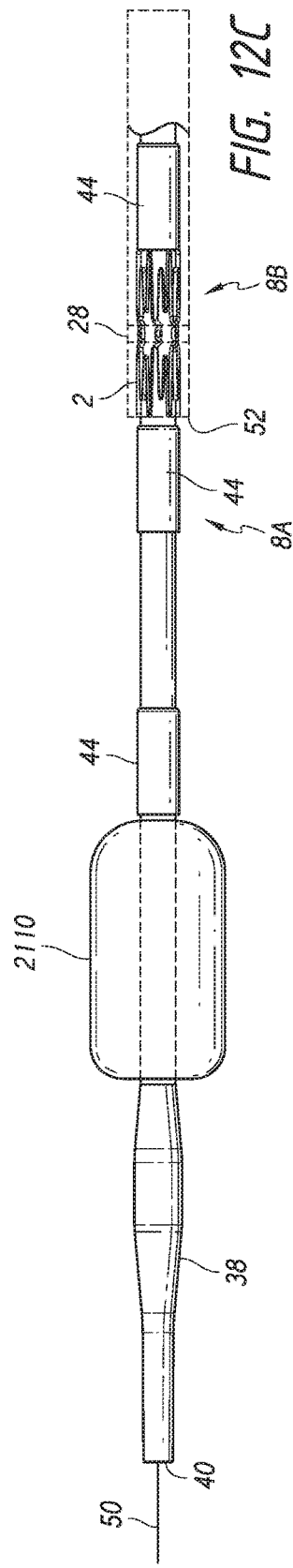

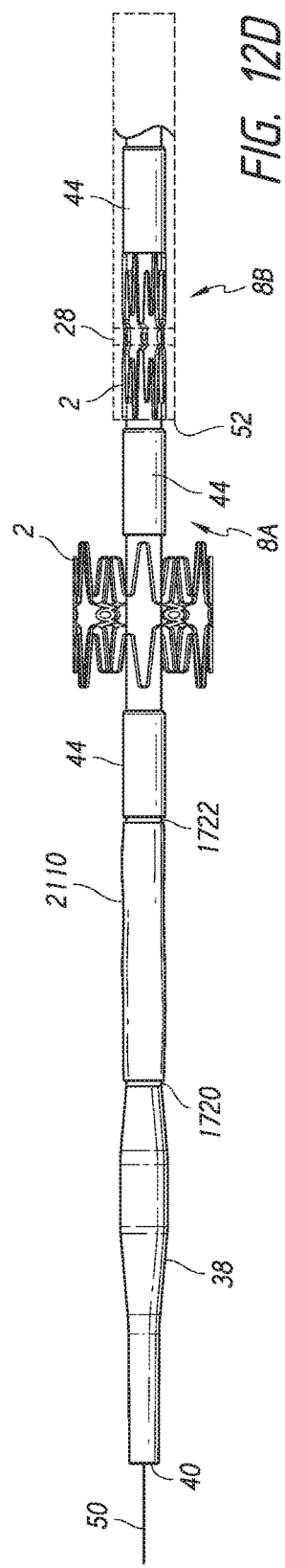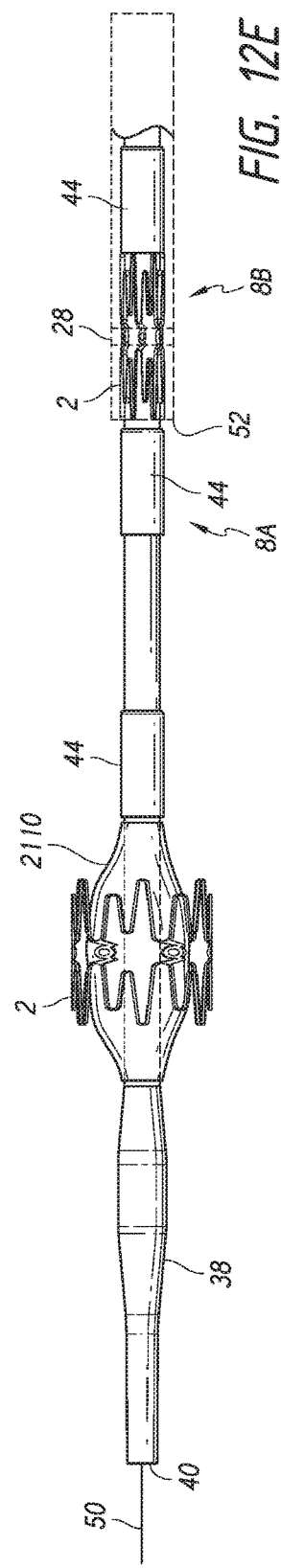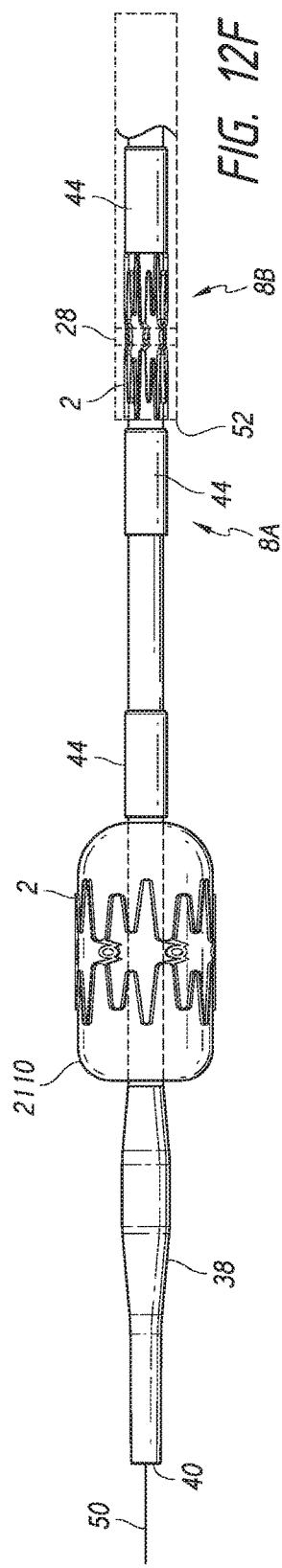

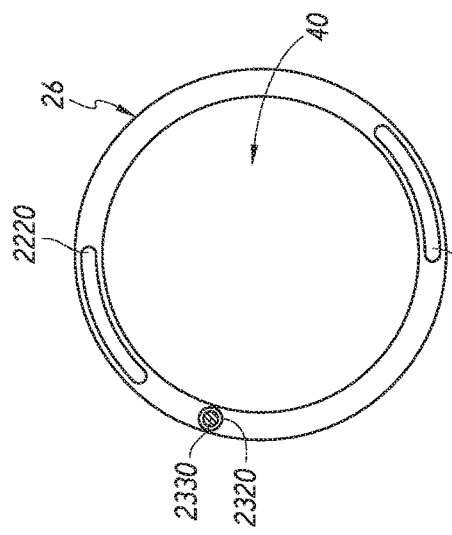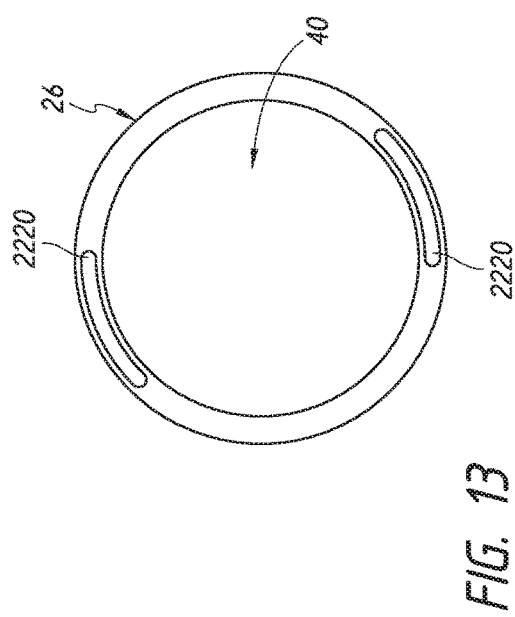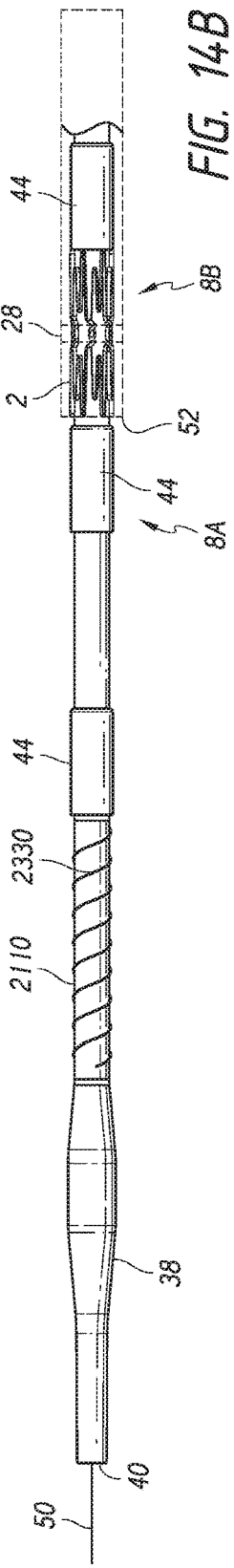

DELIVERY DEVICE AND METHOD OF DELIVERY

INCORPORATION BY REFERENCE TO ANY PRIORITY APPLICATIONS

This application is a continuation of U.S. patent application Ser. No. 15/000,437, filed Jan. 19, 2016 and issued as U.S. Pat. No. 9,433,520, which claims the benefit of priority of U.S. Provisional Appl. No. 62/109,550, filed Jan. 29, 2015, U.S. Provisional Appl. No. 62/109,534, filed Jan. 29, 2015, and U.S. Provisional Appl. No. 62/274,236, filed Jan. 1, 2016. All of the above applications are incorporated by reference herein and are to be considered a part of this specification. Any and all applications for which a foreign or domestic priority claim is identified in the Application Data Sheet as filed with the present application are hereby incorporated by reference under 37 CFR 1.57.

BACKGROUND

Field of the Invention

Disclosed herein are delivery devices and methods of delivery. Certain embodiments are described with reference to sequential delivery of multiple intraluminal devices from a delivery device. The delivery devices and methods can be used in procedures to treat atherosclerotic occlusive disease, though they are not limited to these procedures.

Description of the Related Art

There are a number of medical conditions and procedures in which a device such as a stent is placed in the body to create or maintain a passage. There are a wide variety of stents used for different purposes, from expandable coronary, vascular and biliary stents, to plastic stents used to allow the flow of urine between kidney and bladder.

Stents are often placed in the vascular system after a medical procedure, such as balloon angioplasty. Balloon angioplasty is often used to treat atherosclerotic occlusive disease. Atherosclerotic occlusive disease is the primary cause of stroke, heart attack, limb loss, and death in the US and the industrialized world. Atherosclerotic plaque forms a hard layer along the wall of an artery and can be comprised of calcium, cholesterol, compacted thrombus and cellular debris. As the atherosclerotic disease progresses, the blood supply intended to pass through a specific blood vessel is diminished or even prevented by the occlusive process. One of the most widely utilized methods of treating clinically significant atherosclerotic plaque is balloon angioplasty, which may be followed with stent placement.

SUMMARY

Currently available stents and stent delivery systems have many limitations and drawbacks. There exists a continuing need for improvement in intraluminal devices and associated delivery devices.

According to certain embodiments, a delivery device can be provided for sequential delivery of a plurality of intraluminal devices (e.g., stents, tacks, staples, etc.) held in a compressed state on the delivery device. For purposes of this disclosure the word tack will be used to describe one of many intraluminal devices which can be deployed from a delivery device. The delivery device can comprise a plurality of delivery platforms, the delivery platforms configured for holding a tack in a compressed position on the delivery device and having a unique shape, such as a non-constant outer diameter, an hourglass shape, a tapered proximal half, ridges, dimples, etc. This unique shape can be positioned between annular pusher bands that may also be radiopaque markers.

In some embodiments, the unique shape is provided by a sleeve of flexible material with the unique shape surrounding a harder inner shaft. Further, the annular pusher bands can be made of wire or sections of material to increase flexibility while remaining radiopacity.

A tack deployment method can include alignment of radiopaque markers on the outer sheath and the tack to be deployed prior to deployment.

A method of marker band alignment and intraluminal device or tack delivery can be performed. The method can include: advancing a delivery device with a plurality of tacks in a compressed state to a treatment area; each tack comprising a plurality of struts and a radiopaque marker positioned in a central region of the tack, each tack being a same size with the radiopaque marker positioned in a same location; the delivery device comprising an inner core having a plurality of delivery platforms, each delivery platform having one of the plurality of tacks, and an outer sheath covering the inner core and the delivery platforms, the outer sheath having a radiopaque marker band positioned proximally from a distal end; withdrawing the outer sheath until the radiopaque marker band on the outer sheath and radiopaque marker on a first tack to be delivered are aligned; aligning these two radiopaque markers with a treatment area such as a tissue dissection or lesion to be treated before release of the tack; then withdrawing the outer sheath to release the tack.

In some embodiments, a delivery device can comprise an inner shaft, a delivery platform and an outer sheath. The delivery platform can include a pair of annular bands around the inner shaft, both of the annular bands having a first outer diameter and a sleeve. The sleeve can be secured to the inner shaft and positioned between the annular bands. The sleeve can have a lower durometer than the inner shaft and optimally also lower than the pair of annular bands. The sleeve can further have a non-constant outer diameter being less than the first outer diameter of the annular bands. The delivery platform can be configured to receive an intraluminal device for deployment from the delivery device into a vessel and to receive the intraluminal device between the annular bands and on the sleeve. The outer sheath can be positioned on and slidable over the inner shaft and the delivery platform, the outer sheath having a pre-deployment position covering the delivery platform and at least one delivery position where the outer sheath is withdrawn exposing at least one of the annular bands and the sleeve of the delivery platform.

According to some embodiments, a plurality of additional delivery platforms can be included for sequential delivery of a plurality of intraluminal devices. Each additional delivery platform can comprise an additional sleeve and an additional annular band. Each of the annular bands can have a radius on a proximal end and/or comprise a radiopaque helical coil. The radiopaque helical coil can be encased in a polymer having a higher durometer than a polymer that forms the sleeve.

The sleeve can include any number of different shapes and sizes, and can include ridges, dots, dimples, etc.

In some embodiments, a delivery device can comprise an inner shaft, the inner shaft having a nose cone on the distal tip; a delivery platform; and an outer sheath. The delivery platform can comprise a pair of annular bands secured to the inner shaft, both of the annular bands having a first outer diameter; and a sleeve secured to the inner shaft and positioned between the annular bands. The sleeve can have a lower durometer than the inner shaft and optionally also the pair of annular bands. The sleeve may further have a first constant outer diameter section and a second constant outer diameter section having a larger outer diameter than the first, but less than the first outer diameter of the annular bands, and the second constant outer diameter section having a shorter axial length than the first constant outer diameter section, the sleeve further having a smooth tapered transition between the first and second constant outer diameter sections. The delivery platform can be configured to receive an intraluminal device for deployment from the delivery device into a vessel and configured to receive the intraluminal device between the annular bands and on the sleeve. The outer sheath can be positioned on and slidable over the inner shaft and the delivery platform. The outer sheath can have a pre-deployment position covering the delivery platform and at least one delivery position where the outer sheath is withdrawn exposing at least one of the annular bands and the sleeve of the delivery platform.

In some embodiments, a delivery device can comprise an inner shaft, a distal annular band, a proximal annular band, a delivery platform, an outer sheath, and a post dilation deployment device. The distal annular band and the proximal annular band can be surrounding and fixed to the inner shaft. The inner shaft can have a first diameter and the distal annular band and the proximal annular band can have a second diameter that is larger than the first diameter (of the inner shaft). The delivery platform can be defined by a proximal end of the distal annular band and a distal end of the proximal annular band. The delivery platform can be configured to receive a self-expanding intraluminal device between the distal annular band and the proximal annular band and around the inner shaft for deployment from the delivery device into a vessel. The outer sheath can be positioned on and slidable over the inner shaft and the delivery platform. The outer sheath can have a pre-deployment position, covering the delivery platform, and at least one delivery position, where the outer sheath is withdrawn exposing the delivery platform and at least one of the distal annular band and the proximal annular band. The post dilation deployment device can comprise a deployment platform and a plurality of expansion filaments. The deployment platform can be fixed with respect to the inner shaft. The plurality of expansion filaments can be radially spaced around the inner shaft. Further, each expansion filament of the plurality of expansion filaments can have a first end fixed with respect to an end of the deployment platform. The plurality of expansion filaments can have a pre-actuated position, having a pre-deployment diameter, and an actuated position, having a deployment diameter larger than the pre-deployment diameter. The post dilation deployment device can be configured to apply a radial force to an inner surface of the self-expanding intraluminal device after deployment of the self-expanding intraluminal device so as to improve at least one of expansion of the self-expanding intraluminal device and seating of the self-expanding intraluminal device in the vessel.

A delivery device can comprise an inner shaft, a delivery platform, an outer sheath, and a post dilation deployment device. The inner shaft can have a nose cone on the distal tip. The delivery platform can be fixed in position on the inner shaft with respect to the nose cone. Furthermore, the delivery platform can comprise a pair of annular bands secured to the inner shaft and a middle portion. Both of the annular bands can have a first outer diameter and the middle portion can have a second outer diameter. The second diameter can be smaller than the first outer diameter. The delivery platform can be configured to receive an intraluminal device for deployment from the delivery device into a vessel. More specifically, the delivery platform can be configured to receive the intraluminal device between the annular bands and on the inner shaft. The outer sheath can be positioned on and slidable over the inner shaft and the delivery platform. The outer sheath can have a pre-deployment position, covering the delivery platform, and at least one delivery position, where the outer sheath is withdrawn exposing at least one of the annular bands and the sleeve of the delivery platform. The post dilation deployment device can be positioned between the nose cone and the delivery platform and can comprise a plurality of expansion filaments. The expansion filaments can be configured to be radially expanded upon actuation so as to generate an outward radial force on an inner surface of the intraluminal device after release of the intraluminal device.

An intraluminal device deployment method can include one or more of the following steps. Advancing a delivery device with a plurality of intraluminal devices in a compressed state to a treatment area. Each of the plurality of intraluminal devices can comprise a plurality of struts and a radiopaque marker positioned in a central region of the intraluminal device. Each of the plurality of intraluminal devices can be a same size with the radiopaque marker positioned in a same location. The delivery device can comprise an inner shaft having a plurality of delivery platforms, each intraluminal device of the plurality of intraluminal devices positioned at a respective delivery platform of the plurality of delivery platforms, and an outer sheath covering the inner shaft and the plurality of delivery platforms, the outer sheath having a radiopaque marker band positioned proximally from a distal end of the outer sheath. Withdrawing the outer sheath until the radiopaque marker band on the outer sheath and radiopaque marker on a first intraluminal device to be delivered of the plurality of intraluminal devices are aligned. Aligning the aligned radiopaque marker band and the radiopaque marker with the treatment area before release of the first intraluminal device. Withdrawing the outer sheath to release the first intraluminal device. Withdrawing the outer sheath until the radiopaque marker band on the outer sheath and radiopaque marker on a second intraluminal device to be delivered of the plurality of intraluminal devices are aligned.

In some embodiments of the method, aligning the aligned radiopaque marker band and the radiopaque marker with the treatment area can comprise centering the aligned radiopaque marker band and the radiopaque marker at a tissue dissection before release of the first intraluminal device. In some embodiments of the method, withdrawing the outer sheath until the radiopaque marker band on the outer sheath and radiopaque marker on the first intraluminal device to be delivered of the plurality of intraluminal devices are aligned can comprise withdrawing the outer sheath until a distal-most end of the outer sheath and a distal-most end of the first intraluminal device are aligned. In some embodiments of the method, withdrawing the outer sheath until the radiopaque marker band on the outer sheath and radiopaque marker on the first intraluminal device to be delivered of the plurality of intraluminal devices are aligned can comprise withdrawing the outer sheath until the radiopaque marker band is positioned at a middle of the first intraluminal device. In some embodiments of the method, the first intraluminal device can have a single column of radiopaque markers and withdrawing the outer sheath until the radiopaque marker band on the outer sheath and radiopaque marker on the first intraluminal device to be delivered of the plurality of intraluminal devices are aligned can comprise withdrawing the outer sheath until the radiopaque marker band encircles the single column of radiopaque markers.

An intraluminal device deployment method can comprise advancing a delivery device with an intraluminal device in a compressed state to a target volume. The delivery device can comprise an inner shaft, a delivery platform, an outer sheath and a post dilation deployment device. The inner shaft can have a first diameter. The delivery platform can have a distal and a proximal annular band each having a second diameter larger than the first diameter (of the inner shaft). The delivery platform can be configured to receive the intraluminal device between the annular bands and around the inner shaft for deployment from the delivery device into a volume. The outer sheath can be positioned about and slidable over the inner shaft and the delivery platform. The outer sheath can have a pre-deployment position, covering the delivery platform, and a deployment position, exposing the delivery platform. The post dilation deployment device can comprise a plurality of expansion filaments configured to be radially expanded upon activation of the post deployment dilation device so as to generate an outward radial force on an inner surface of the intraluminal device after release and expansion of the intraluminal device. The intraluminal device deployment method can further comprise: withdrawing the outer sheath to release the intraluminal device; expanding the intraluminal device; moving the delivery device so as to position at least a portion of the post deployment dilation device within the expanded intraluminal device; and activating the post deployment dilation device to cause at least a portion of the post deployment dilation device to radially expand and to generate an outward radial force on an inner surface of the expanded intraluminal device. The expanding step can comprise one of allowing the intraluminal device to expand and actively expanding the intraluminal device;

BRIEF DESCRIPTION OF THE DRAWINGS

Various embodiments are depicted in the accompanying drawings for illustrative purposes, and should in no way be interpreted as limiting the scope of the inventions, in which like reference characters denote corresponding features consistently throughout similar embodiments.

FIG. 1 is a side view of a delivery device that has been shortened to facilitate illustration.

FIG. 2 shows a view of the distal end of the delivery device with an outer sheath withdrawn.

FIG. 3 shows an embodiment of intraluminal device or tack.

FIG. 3A shows a flattened section of the tack of FIG. 3.

FIG. 4 illustrates a detail view of the distal end of the delivery device with the outer sheath partially withdrawn.

FIGS. 7A-C illustrate certain steps of a deployment method.

FIGS. 8A-8C are various views of a distal end of a delivery device with a post deployment dilation device comprising a plurality of expansion filaments.

FIGS. 8D-8G show steps in a method for using a post deployment dilation device comprising a plurality of expansion filaments.

FIGS. 9A-9B show cross sections of various inner shafts adapted to receive a plurality of expansion filaments.

FIGS. 10A-10C are various views of a distal end of a delivery device with a post deployment dilation device comprising a sliding sleeve and a plurality of expansion filaments.

FIGS. 10D-10F show steps in a method for using a post deployment dilation device comprising a sliding sleeve and a plurality of expansion filaments.

FIGS. 11A-11C are various views of a distal end of a delivery device with a post deployment dilation device comprising a sliding sleeve and a bellow.

FIGS. 11D-11F show steps in a method for using a post deployment dilation device comprising a sliding sleeve and a bellow.

FIGS. 12A-12C are various views of a distal end of a delivery device with a post deployment dilation device comprising an inner core balloon.

FIGS. 12D-12F show steps in a method for using a post deployment dilation device comprising an inner core balloon.

FIG. 13 shows a cross section of an inner shaft having a plurality of fluid lumens adapted to transmit fluid from to an inner core balloon.

FIGS. 14A-14B show a helical filament system for capturing and confining a post-dilated inner core balloon.

DETAILED DESCRIPTION

Figure 5:
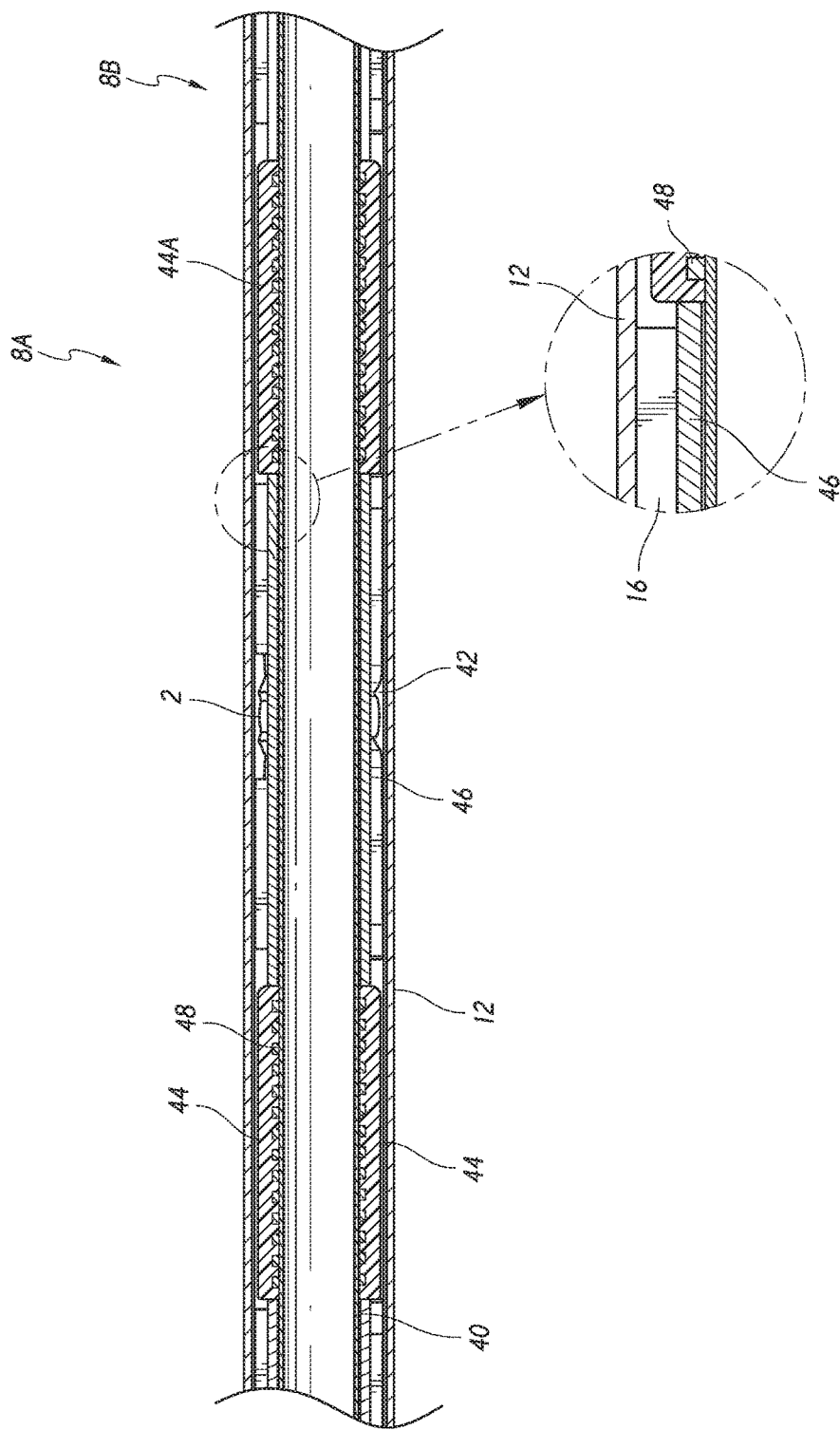
FIG. 5 is a cross section of a delivery device showing an embodiment of delivery platform.

A delivery device 10 can be used as part of a procedure to treat atherosclerotic occlusive disease. The delivery device can be used to deliver one or more intraluminal devices 2, such as tacks, to a site of plaque accumulation. The tacks can stabilize the site and/or hold pieces of plaque out of the way of blood flow. It will be understood that though the delivery devices and methods described herein are described primarily with reference to vascular procedures, they can also be used in treatments for other parts of the body.

FIGS. 1 and 2 illustrate an embodiment of delivery device 10 that can be used for sequential delivery of multiple intraluminal devices 2. The delivery device 10 can be used in procedures to treat atherosclerotic occlusive disease, though it is not limited to these procedures.

The delivery device 10 of FIG. 1, which has been shortened to facilitate illustration, highlights the distal 4 and proximal ends 6. The proximal end 6 can be held by a physician or other medical professional during a medical procedure. It is used to control delivery of one or more intraluminal devices or tacks 2. FIG. 2 shows the distal end 4 with six (6) intraluminal devices 2, each positioned at a dedicated delivery platform 8. Comparing FIGS. 1 and 2, it can be seen that an outer sheath 12 has been withdrawn from the distal end in FIG. 2. This reveals the delivery platforms 8 and the respective intraluminal devices 2. The intraluminal devices 2 are preferably self-expandable and are shown in their compressed position to represent how they would fit in the delivery platforms. In typical use, the outer sheath 12 would be covering the intraluminal devices 2 when in this position. As will be discussed in more detail below, the outer sheath 12 can be withdrawn in a systematic manner to deploy one intraluminal device 2 at a time at a desired treatment location.

Relatively small intraluminal devices 2, for example with only one (FIGS. 3 & 3A) or two columns of cells, can be delivered at precise treatment locations and space appropriately to not overlap. FIG. 3A shows a flattened section of the tack of FIG. 3. It can be seen that a single column of cells 14 are formed by two concentric rings of undulating struts 16 connected by bridge members 18. The bridge members 18 have a pair of anchors 20 and a radiopaque marker 22. The intraluminal device can also be comprised of two or more cells, or alternatively by other structures known in the art. Multiple small intraluminal devices 2 can be used to treat a single or multiple lesions. This can minimize the amount of foreign material in the body, while providing needed holding forces. Various embodiments of intraluminal devices and delivery devices are described in more detail in Applicants' related patent application Ser. No. 13/179,458 filed Jul. 8, 2011, published as US 2012/0035705 and patent application Ser. No. 13/749,643 filed Jan. 24, 2013, published as US 2013/0144375, both of which are incorporated by reference herein and made a part of this specification.

It will be understood, that the delivery devices and methods can also be used for other intraluminal devices 2, including larger devices, and are not limited to use with intraluminal devices 2 having only one or two columns of cells.

Returning now to FIG. 1, the proximal end 6 of the illustrated embodiment will now be described. The delivery device 10 can include an outer sheath 12, a proximal housing 24, and an inner shaft 26. The outer sheath 12 can be constructed as a laminate of polymer extrusions and braided wires embedded in the polymer extrusions. Flexibility and stiffness can be controlled through the number of braid wires, the braid pattern and pitch of the braid. In other embodiments, the outer sheath can be formed of a hypotube, such as a metal or plastic hypotube. Flexibility and stiffness of the sheath can be controlled by many features such as the slope and frequency of a spiral cut along the length of the hypotube. The outer sheath may also include a radiopaque (RO) marker 28 at or near the distal end. In some embodiments, the radiopaque marker 28 can be an annular band spaced from the distal-most end.

As shown, the outer sheath 12 is a braided shaft and the proximal housing 24 is a bifurcation luer that connects to the outer sheath through a strain relief 30. The strain relief 30 can take any form, such as being made of polyolefin or other similar material.

The bifurcation luer 24 has a main arm to receive the inner shaft 26 and a side arm. The bifurcation luer can be disposed at the proximal end of the outer sheath. The side arm includes a flushing port that is used to flush out air and increase lubricity in the space between the sheath and the inner shaft.

A tuohy borst adapter, hemostatic valve, or other sealing arrangement 32 can be provided proximal of or integrated into the bifurcation luer 24 to receive and seal the proximal end of the space between the inner shaft 26 and the outer sheath 12. The tuohy borst adapter can also provide a locking interface, such as a screw lock, to secure the relationship between the outer sheath and the inner shaft. This can allow the physician to properly place the distal end without prematurely deploying a tack.

The inner shaft is shown with a proximal luer hub 34 and deployment reference marks 36. The deployment reference marks 36 can correspond with the delivery platforms 8, such that the spacing between each deployment reference mark can be the same as the spacing between features of the delivery platforms. For example, the space between deployment reference marks can be the same as the distance between the centers of the delivery platforms.

In some embodiments, a distal most deployment reference mark, or a mark that is different from the others, such as having a wider band or different color, can indicate a primary or home position. For example a deployment reference mark with a wider band than the others can be aligned with the proximal end of the bifurcation luer 24 or hemostatic valve 32. This can indicate to a physician that the outer sheath is in a position completely covering the inner shaft 26 proximal of the nose cone 38. In some embodiments, this alignment can also translate to alignment of the RO marker 28 on the outer sheath to a RO marker on the distal end of the inner shaft 26.

In some embodiments, one or more of the deployment reference marks 36 can represent the number of tacks that are within the system. Thus, once a tack is released, the deployment reference mark 36 will be covered up and the physician can know that the remaining deployment reference marks correspond with the remaining number of tacks available for use. In such an embodiment, the proximal end of the bifurcation luer 24 or hemostatic valve 32 can be advanced to be centered approximately between two reference marks to indicate deployment. It will also be understood that the delivery device could have a handle or trigger assembly such as those described in U.S. Provisional Appl. No. 62/109,550, filed Jan. 29, 2015, and U.S. Pat. No. 9,192,500, both of which are incorporated by reference herein and are to be considered a part of this specification.

Looking now to FIG. 4, a detail view of the distal end 4 of the delivery device 10 is shown. Features of the illustrated embodiment include the inner shaft 26 with a distal soft tip 38. The tip 38 can be a tapered nose cone. The nose cone 38 serve as a dilating structure to atraumatically displace tissue and help to guide the delivery device through the vasculature. The tip 38, itself, may be radiopaque, or a radiopaque element 27 can be incorporated into or near the tip. A guidewire lumen 40 can be seen that extends through the inner shaft 26 to the proximal luer hub 34 (FIG. 1). The guidewire lumen 40 is configured for receipt and advancement of a guidewire therein.

Parts of a delivery platform 8 are also shown. The delivery platforms 8 are identical in the illustrated embodiment, though other embodiments can have different sizes and constructions between different delivery platforms. A crimped or compressed tack 2 is shown in the delivery platform 8.

As can be seen in FIGS. 2 and 4, one or more delivery platforms 8 can be disposed on the inner shaft 26 adjacent the distal end 4 of the delivery device 10. Each of the delivery platforms 8 can comprise a recess 42 extending positioned between a pair of annular pusher bands 44. FIG. 5 shows a cross section of a delivery device at one embodiment of delivery platform 8A. In the illustrated embodiment, the proximal annular pusher band 44A of a first platform 8A is also the distal annular pusher band 44A of the platform 8B located immediately proximal (only partially shown). The annular pusher band 44 has a larger outer diameter as compared to the delivery platform at the recess 42. In some embodiments, the recess can be defined as the smaller diameter region next to, or between, one or two annular pusher bands and/or an additional feature on the inner shaft 26.

One or more of the annular pusher bands 44 can be radiopaque marker bands. For example, proximal and distal radiopaque marker bands 44 can be provided to make the ends of the platform 8 visible using standard visualization techniques. The annular marker bands 44 can take any suitable form, for example including one more of tantalum, iridium, and platinum materials. In some embodiments, the pusher bands 44 can be 4 mm long with 6.75 mm recesses between them. A tack of 6.5 mm can be positioned between the pusher bands 44. In some embodiments, the pusher bands can be between 50-70% of the size of the recess and/or the tack. In some embodiments, the pusher bands are about 60%. In other embodiments, the pusher bands can be much smaller, at between 10-20% of the size of the recess and/or the tack. This may be the case especially with longer tacks. In some embodiments, at least the proximal ends of the pusher bands 44 can have a radius to help reduce potential for catching on deployed tacks during retraction of the delivery device.

Reducing the difference in length between the recess and the tack can increase the precision of placement of the tack, especially with tacks having only one or two columns of cells. In some embodiments, the recess can be less than 1, 0.5, 0.4, 0.3, 0.25, or 0.2 mm longer than the tack. The tack can be any number of different sizes, such as 4, 5, 6, 6.5, 8, 10, or 12 mm in length.

The outer sheath 12 can be made of polyether block amide (PEBA), a thermoplastic elastomer (TPE) available under the trade name PEBAX. In some embodiments, the outer sheath 12 can have a thinner inner liner made of a polytetrafluoroethylene (PTFE) such as TEFLON. Any radiopaque marker band(s) 28 or other radiopaque material may be positioned between these two layers. In other embodiments, the radiopaque marker band(s) 28, or other radiopaque material can be embedded within one or more layers of the outer sheath 12. The radiopaque marker band(s) 28 can range from 0.5 mm to 5 mm wide and be located from 0.5 mm to 10 mm proximal from the distal-most tip 52. In some embodiments, the radiopaque marker band(s) 28 can be 1 mm wide and 3 mm proximal from the distal-most tip 52.

In the cross section of FIG. 5 it can be seen that a sleeve 46 is positioned around the inner shaft 26 between the two annular bands 44. In some embodiments, a delivery platform 8 can comprise a sleeve 46 surrounding a shaft 26, where the sleeve 46 is made of a different material, or has different material properties, than the shaft 26. In some embodiments, the sleeve provides a material having a tackiness, a grip, a tread pattern, and/or other features to help the tack stay in place in the delivery platform. In some embodiments, the sleeve can be made of PEBA. The inner shaft according to some embodiments is a composite extrusion made of a PTFE/polyimide composite. The sleeve can be softer than (a lower durometer than) the inner shaft and/or the pusher bands 44. This may be the case even if made of similar types of materials. In some embodiments, the sleeve can be a material having a tackiness, a grip, a tread pattern, and/or other features to help the tack stay in place (e.g. longitudinal position with respect to the inner shaft) while the outer sleeve 12 is withdrawn. This can increase the amount of control during deployment and reduce the likelihood that the tack will shoot out distally from the delivery platform (known in the industry as watermelon seeding). In some cases the outer sheath can be partially removed thereby partially exposing an intraluminal device whereby the intraluminal device can partially expand while being securely retained by the delivery prior to full release.

The sleeve 46 can be sized so that with the tack 2 in the delivery platform 8 there is minimal to no space between the tack and the outer sheath. In some embodiments, the sleeve 46 can be co-molded with or extruded onto the inner shaft 26. In some embodiments, the delivery device 10 can be formed with a single sleeve 46 extending over a length of the inner shaft 26. For example, the sleeve can extend from the first delivery platform to the last delivery platform. The annular bands 44 may surround distinct sections of sleeve 46, or they may be encased by the sleeve 46. In some embodiments, each delivery platform 8 has a separate sleeve 46 positioned in the recess 42. The annular bands 44 may be encased by a different material, or may not be encased at all.

Figure 6A:
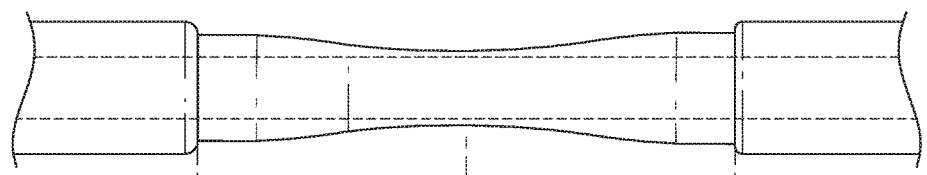
FIGS. 6A-E illustrate various embodiments of delivery platforms having different shapes.
Figure 6B:
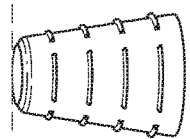
Figure 6C:
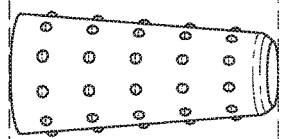
Figure 6D:
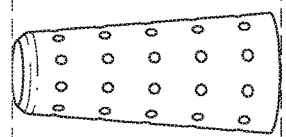

As will be understood from FIG. 5, the sleeve 46 can be cylindrical with a circular cross-section that is maintained across a portion of or the entire length of sleeve. In other embodiments, the sleeve has a unique shape and may include one or more of the following: tapering (FIGS. 6A-E), an hourglass shape (FIG. 6A), ridges (FIG. 6B), dimples (FIG. 6C), dots (FIG. 6D), two or more different diameters (FIG. 6E), etc. Features such as ridges, dots, and dimples can be positioned in number of different patterns or groupings. In addition, the sleeve (FIGS. 6B-D), or a section of the sleeve (FIG. 6E) can extend along less than the entire recess. In some embodiments, the length of the sleeve or larger outer diameter section can correspond to the length of the tack. For example, the sleeve or larger diameter section can extend ¾, ⅔, ½, ⅖, ⅓, ¼ of the recess and/or tack. Further, the length of the sleeve or larger outer diameter section can be related to the size of struts in the undulating ring 16, such as a proximal most undulating ring. For example, it can extend along the entire, ⅘, ¾, ⅔, or ½ of the length of a strut or the length of the proximal most undulating ring. A short sleeve, or a larger outer diameter section of a sleeve, preferably extends from the proximal end of the recess distally (FIGS. 6D-E), but can also be centered in the recess, positioned on at the distal end (FIG. 6C), or at other positions within the recess.

Figure 6E:
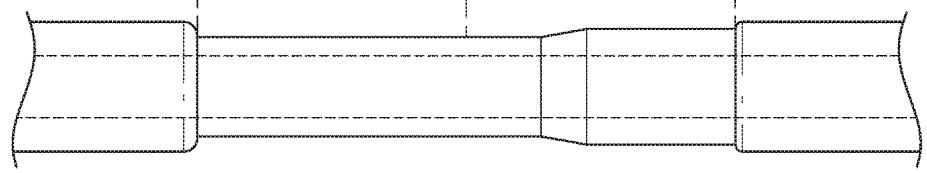

The sleeve of FIG. 6E is shown having two different constant outer diameter sections with a short taper between them. The sleeve can be formed from two separate sections that are thermally bonded together. The tapered portion can also be created by thermal bonding so that there is a smooth transition between the two constant outer diameter sections. As has been mentioned, the larger constant outer diameter section preferably extends from the proximal end of the recess distally. This larger outer diameter section that may or may not have a constant outer diameter can extend along less than the entire recess as has been discussed above.

In some embodiments, an inner shaft 26 can have a lower durometer sleeve 46 between pushers 44. A tack 2 can be crimped onto the sleeve 46 and an outer sheath 12 can constrain the crimped tack in place. The clearance between the sleeve 46 and the outer sheath 12 can result in a slight interference fit between the crimped tack 2 and the inner and outer elements. This slight interference allows the delivery system to constrain the crimped tack during deployment until it is almost completely unsheathed allowing the distal portion of the tack to "flower petal" open and engage the vessel wall, reducing the potential for jumping.

According to some embodiments, the inner shaft 26 can be made of a polyimide-PEBA combination and the lower durometer PEBA sleeve 46 can be thermally bonded in between pushers 44. A tack 2 can be crimped onto the sleeve 46 and a PTFE lined outer sheath 12 can constrain the crimped tack in place.

Returning to FIG. 5, a feature of certain embodiments of radiopaque marker band 44 is shown. As has been mentioned, the sleeve 46 may encase the annular bands 44. Alternatively, another material can encase the metallic bands to form the annular marker bands 44. The annular marker bands 44 can be made of wire 48 or multiple pieces of material or having slits to increase flexibility while remaining radiopacity. In some embodiments the wire can form a helical coil that is wrapped around the inner shaft 26.

Moving now to FIGS. 7A-C, certain methods of deployment will now be described. A delivery device 10 can be used as part of a procedure to treat atherosclerotic occlusive disease. The delivery device can be used to deliver one or more intraluminal devices 2, such as tacks, to a site of plaque accumulation. The tacks can stabilize the site and/or hold pieces of plaque out of the way of blood flow.

The tacks are preferably self-expandable. Thus, withdrawing the sheath 12 to reveal a tack 2 allows the tack to deploy from the delivery device 10 by self-expansion. The sheath can be withdrawn in small increments to sequentially deliver tacks at desired locations in a blood vessel. In some embodiments, the small increments can correspond with the deployment reference marks 36. The deployment reference marks 36 can be spaced apart at least the length of the tack, so that each tack can be deployed at once, rather than the gradual release typical of a longer stent. This can allow for more precise placement of the tack.

Balloon angioplasty is an accepted method of opening blocked or narrowed blood vessels in every vascular bed in the body. Balloon angioplasty is performed with a balloon angioplasty catheter. The balloon angioplasty catheter consists of a cigar shaped, cylindrical balloon attached to a catheter. The balloon angioplasty catheter is placed into the artery from a remote access site that is created either percutaneously or through open exposure of the artery. The catheter is passed along the inside of the blood vessel over a wire that guides the way of the catheter. The portion of the catheter with the balloon attached is placed at the location of the atherosclerotic plaque that requires treatment. The balloon is inflated to a size that is consistent with the original diameter of the artery prior to developing occlusive disease. In some instances the balloon is coated with, or otherwise configured to deliver, a drug or biologic to the tissue. When the balloon is inflated, the plaque is broken. Cleavage planes form within the plaque, permitting the plaque to expand in diameter with the expanding balloon. Frequently, a segment of the plaque is more resistant to dilatation than the remainder of the plaque. When this occurs, greater pressure pumped into the balloon results in full dilatation of the balloon to its intended size. The balloon is deflated and removed and the artery segment is reexamined. The process of balloon angioplasty is one of uncontrolled plaque disruption. The lumen of the blood vessel at the site of treatment is usually somewhat larger, but not always and not reliably.

Some of the cleavage planes created by fracture of the plaque with balloon angioplasty can form a dissection. More generally, a dissection occurs when a portion of the plaque or tissue is lifted away from the artery, is not fully adherent to the artery and may be mobile or loose. The plaque or tissue that has been disrupted by dissection protrudes into the flow stream. If the plaque or tissue lifts completely in the direction of blood flow, it may impede flow or cause acute occlusion of the blood vessel. There is evidence that dissection after balloon angioplasty must be treated to prevent occlusion and to resolve residual stenosis. There is also evidence that in some circumstances, it is beneficial to place a metal retaining structure, such as a stent or other intraluminal device to hold open the artery after angioplasty and/or force the dissected material back against the wall of the blood vessel to create an adequate lumen for blood flow.

A variety of delivery methodologies and devices can be used to deploy an intraluminal device, such as a tack 2, some of which are described below. For example, a tack can be delivered into the blood vessel with an endovascular insertion. The delivery devices for the different embodiments of plaque tacks can be different or the same and can have features specifically designed to deliver the specific tack. The tack and installation procedure may be designed in a number of ways that share a common methodology of utilizing an expansion force of the delivery mechanism (such as balloon expansion) and/or the expansion force of an undulating ring to enable the tack to be moved into position in the blood vessel, then released to an expanded state within the blood vessel. A tack deployment method can include alignment of radiopaque markers on the outer sheath and the tack to be deployed prior to deployment.

Referring now FIG. 7A, a delivery device 10 with an outer sheath 12 is shown in a first pre-deployment state. Multiple tacks 2 can be held by the outer sheath 12 in a compressed state within the delivery device 10. In some embodiments, the tacks 2 are flash frozen in their compressed state to facilitate loading onto the delivery device. The tacks can extend over a given length of the delivery device as has been described.

The delivery device can be advanced over a guidewire 50 in a patient's vasculature to a treatment site. The guidewire 50 can be the same guidewire used in a prior step of a procedure, such as the guidewire used to position an angioplasty balloon. Once positioned at the treatment location, the outer sheath 12 can be withdrawn or retracted to second pre-deployment position (FIG. 7B). The second pre-deployment position can be used to adjust the position of the outer sheath to account for any stretching, tortuosity, etc. that may require some adjustment before releasing a tack. In the second pre-deployment position, the distal end 52 of the outer sheath can be positioned at, or slightly distal of the distal end of a tack to be deployed.

According to some embodiments, the outer sheath 12 can have a radiopaque annular marker band 28 and the tack can also have one or more radiopaque markers 22. The radiopaque markers 22 can be positioned in a column around the tack. The distance "L" from the distal end of the tack to the radiopaque marker 22 can be the same as the distance from the distal end 52 of the outer sheath 12 to the radiopaque annular marker band 28. In some embodiments, this distance is to the center of the markers 22 and marker band 28. In some embodiments, the length "L" on the outer sheath is at least as long as the length "L" on the tack, if not slightly longer. The outer sheath can be free from other radiopaque markers. In addition, the tack can also be free from other radiopaque markers or columns of radiopaque markers. Thus, the outer sheath can have only a single marker band 28 at the distal end that is spaced from the distal-most end 52 of the outer sheath 12 by at least a distance from the distal-most end of the tack 2 to a radiopaque marker 22 or column of radiopaque markers. In the illustrated embodiment, the radiopaque marker 22 or column of radiopaque markers are positioned in the middle of the device. The radiopaque markers are also positioned on bridge members 18 that connect adjacent rings of undulating struts 16. In some embodiments, the radiopaque marker 22 or column of radiopaque markers can be spaced from the distal-most end of the tack by at least one ring of undulating struts 16. In the illustrated embodiment, the radiopaque marker 22 or column of radiopaque markers is not at the distal-most end of the tack 2, but is spaced therefrom.

Having corresponding radiopaque markers 22, 28 on the tack and the outer sheath can allow the physician to align the markers 22, 28 prior to deployment of the tack. Further, the physician can align the aligned markers with the desired area to be treated. As will be understood, all of this alignment can be done using standard visualization techniques. As has been mentioned, the annular pusher bands 44 on the inner shaft can also be radiopaque. In some embodiments, the pusher bands 44 can be identical and can appear different under visualization than both the marker on the outer sheath and the marker on the tack. Thus, it can be clear to the physician where all of the markers are and which is which. For example, the pusher bands 44 can be axially longer than the marker 28 on the outer sheath and the marker on the tack. Further, the markers on the delivery device can be bands, while the marker(s) on the tack can be dots.

Looking to FIG. 7B, it can be seen that the marker 28 on the outer sheath 12 and the markers 22 on the first tack 2 are aligned and that the distal end of the sheath is positioned at the distal end of the first tack. The delivery device can now be positioned with respect to the lesion for treatment, such as by centering the radiopaque markers at desired location. The sheath can then be withdrawn to place the tack in the desired location.

In some embodiments, the delivery device can have a marker band on the outer sheath positioned proximally from the distal end-one at least half the length of the tack, the tack having a single column of markers at the middle of the device. A method of deployment can include withdrawing the outer sheath until the marker on the outer sheath and the tack to be delivered are aligned, and then aligning these two markers with the middle of the lesion to be treated (or other treatment area) before release of the tack, the release being affected by further withdrawing the outer sheath. It will be understood that markers on the pusher bands 44 can also be used to help align the delivery device before deployment.

The method can be repeated to deliver multiple tacks (see FIG. 7C with tack shown in the compressed state for reference only). In between tack deployment, the delivery device may be moved to a completely different lesion or treatment area, or simply repositioned to ensure space between adjacent tacks once placed.

As discussed previously, in some embodiments, simultaneous placement of the entire tack can result upon release of the tack from the delivery device. Further, multiple tacks can placed as desired in a distal to proximal placement within the treatment segment of the vessel.

In some embodiments an expandable tack, such as that shown in FIGS. 3 & 3A, can exert a relatively constant force to a wide range of vessel lumen diameters, thereby allowing a single delivery catheter to deploy multiple tacks to varying sized vessels. Ideally the tack can be designed to treat vessels ranging in size from 2 to 8 mm, although other sized tacks could be delivered. It is desirable that the force applied by the tack to the vessel varies 5N or less over a 3 mm expansion range. More ideally the force applied will vary 1.5N or less over a 3 mm expansion range.

There are instances where drug coated balloons are being used as an alternative to placing a stent in the vessel. The balloon can dilate narrowing in the vessel and the drug helps to minimize post inflation inflammatory response which can lead to a re-narrowing of the artery. There is clinical evidence that the combination of a balloon and drug can provide an alternative to the implantation of a typical stent which have been historically used to provide both short term and long term scaffolding. Drug coated balloons are desirable in that there is no long term implant placed in the vessel. There are instances however when the expansion of a drug coated balloon may cause damage to the vessel in the form of a tissue dissection in which case a flap or piece of tissue extends into the lumen of the vessel. The dissection can occur within the balloon treatment zone as well as outside of or adjacent to the treatment zone. In these instances it is helpful to tack the dissected tissue against the arterial wall.

A tack having a low outward force can beneficially be used to treat the dissection where a stent may not be appropriate, or desirable.

In some embodiments, the precise placement of the tack can be set upon positioning of the catheter within the vessel based on the position of a marker. Once positioned, one or more tacks can then be deployed while maintaining the catheter in place and slowly removing the outer sheath.

In some embodiments, one or more tacks can be deployed at a dissection of tissue. When an angioplasty procedure is performed there are typically one of three outcomes: 1) an optimal outcome, no further stenting or over treatment needs to be performed, 2) residual stenosis, usually requiring the placement of a stent to prop open or scaffold the vessel so that it remains open and does not return to the prior occluded or partially occluded state, and 3) a tissue dissection. A tissue dissection can be where the vessel experiences trauma such as the disruption of an arterial wall resulting in separation of the intimal layer. This may or may not be flow limiting. One or more tacks can beneficially be deployed at such a tissue dissection. Small tacks allow for the treatment of a subset of the portion of the blood vessel treated by the balloon angioplasty procedure thereby providing a treatment therapy with does not require the implantation of long metal stents over the entire angioplasty treatment area. Ideally, one or more tacks could be used to treat 60% or less of the length of vessel in the angioplasty treatment area. Small tacks having a single (illustrated) or double column of cells, have been shown to cause less injury and to have shorter recovery times than commonly available stents in treating tissue dissections.

Upon placement of the tack, an intravascular construct is formed in situ. The in situ placement can be in any suitable vessel, such as in any peripheral artery. The construct need not be limited to just two tacks. In fact, a plurality of at least three intravascular tacks can be provided in an intravascular construct formed in situ. In one embodiment each tack has a length of no more than about 8 mm, e.g., about 6 mm in an uncompressed state. In one configuration, at least one of, e.g., each of, the tacks are spaced apart from an adjacent tack by at least about 4 mm, or between about 4 mm and 8 mm or between about 6 mm and 8 mm. Although certain embodiments have a length of 8 mm or less, other embodiments can be longer, e.g., up to about 12 or 15 mm long. Also, neighboring tacks can be positioned as close as 2 mm apart, particularly in vessels that are less prone to bending or other movements. In some embodiments, a delivery device can be preloaded with six tacks, each about 6.5 mm long, and can be used to treat lesions up to 15 cm in length.

In the various delivery devices described herein, the spacing between implanted tacks can be controlled to maintain a set or a minimum distance between each tack. As can be seen, the delivery devices and/or tacks can include features that help maintain the desired distance between tacks. Maintaining proper inter-tack spacing can help ensure that the tacks are distributed over a desired length without contacting each other or bunching up in a certain region of the treated vessel. This can help to prevent kinking of the vessel in which they are disposed.

While a three tack construct formed in situ may be suitable for certain indications, an intravascular construct having at least 5 intravascular tacks may be advantageous for treating loose plaque, vessel flaps, dissections or other maladies that are significantly more elongated (non-focal). For example, while most dissections are focal (e.g., axially short), a series of dissections may be considered and treated as a more elongated malady.

In some cases, even shorter axial length tacks can be used to treat even more spaced apart locations. For example, a plurality of tacks, each having a length of no more than about 7 mm, can be placed in a vessel to treat a tackable malady. At least some of the tacks can be spaced apart from an adjacent tack by at least about 5 mm. In some cases, it may be preferred to provide gaps between adjacent tacks that can range from about 6 mm to about 10 mm.

Once the vascular implants, e.g., tacks 2, are placed, there may be areas of the implant that are not fully apposed to the native vessel wall. This may be due to inner lumen wall surface irregularities. Areas where the implant is not fully apposed to the luminal surface may lead to suboptimal hemodynamic flow. Therefore, optionally, to ensure full apposition of the deployed vascular implant, e.g., tack 2, a device may be inserted to further expand the tack 2. For example, a balloon catheter may be introduced for post-deployment dilation, positioned within the tack 2, and then dilated to gently force the struts of the tack 2 against the luminal wall.

Using a separate device, such as the original, or a new, angioplasty balloon, to expand the tacks to the desired state of expansion, as just discussed, requires placing the tack 2 with the delivery device 10, removing the delivery device 10, inserting a new device (e.g., a new balloon or the angioplasty balloon, dilating the new device to expand the tack 2, deflating the new device, and removing the new device from within the vasculature. This additional catheter exchange results in more procedure time and cost, and creates the potential for undesirable interactions with the implants, such as dislodgement, and the potential for vessel wall injury.

Therefore, some embodiments of the delivery device 10 include a portion for post-deployment dilation of the tack 2. Various embodiments an implant delivery system are disclosed that comprise various post deployment dilation devices that provide an integrated dilatation feature (e.g., a mechanical dilation feature). The dilation feature can be used to ensure optimal implant anchoring and circumferential implant apposition to the vessel inner lumen following deployment of a self-expanding vascular implant. Advantages offered by onboard post deployment dilation devices may include: deployment of a plurality of self-expanding implants; elimination of catheter exchanges needed for post-dilatation of a self-expanding implant and the difficulties and risks associated with the exchange procedure; reduction or elimination of the cost associated with consuming an additional balloon catheter for post-dilation of the implant; shortening procedure durations; and reducing ultimate costs.

The delivery device can be the same as the other delivery devices discussed herein with the addition of a post deployment dilation device. The post deployment dilation device can include an expansion element and an expansion control 1730. The expansion element can take a number of forms, including, for example, expansion filaments 1710, 1910, a bellow 2010, or inner core balloon 2110. In some embodiments, the expansion element comprises a movable frame where one end of the frame is configured to move towards the other end to thereby expand the frame. The frame can be made of expansion filaments 1710, 1910, or a bellow 2010, among other designs. The expansion element can be positioned in a deployment platform.

The expansion control 1730 can be positioned at the proximal end of the delivery device 10 and may be actuated by a user to control expansion of the expansion element. In some embodiments, the expansion control 1730 can be a trigger, a cable, or an end of one or more filaments.

The post deployment dilation device can include one or more radiopaque markers, such as bands or rings 1720, 1722. The one or more radiopaque markers can be at one or more ends, the center, or at other locations of the post deployment dilation device. The one or more radiopaque markers may also be movable with the expansion of the expansion element. In some embodiments, the distal most annular pusher band 44 on the inner shaft can define the proximal end of the post deployment dilation device. The nose cone 38 can define the distal end of the post deployment dilation device. As both the nose cone 38 and the pusher band 44 can be radiopaque, the post deployment dilation device may not include any additional radiopaque markers.

Generally speaking, the delivery device 10 may include one or more delivery platforms, as described herein, which may be exposed by the proximal axial sliding of an outer sheath 12 (they alternatively may be covered by the distal axial sliding of an outer sheath 12). The delivery platforms are configured to accept and hold one or more intraluminal devices (e.g., self-expanding tacks 2). The intraluminal devices may be released or deployed within a volume, such as a blood vessel, by withdrawing the outer sheath 12 to expose the delivery platform. In addition to the delivery platforms that are configured to hold and then release one or more (e.g., a plurality) or intraluminal devices, the delivery device 10 may include a post deployment dilation device.

As disclosed herein, post deployment dilation devices are part of the delivery device 10, at least a portion of which may be positioned within a deployed or already-expanded intraluminal device (e.g., a self-expanding tack 2 that has been allowed to expand). The post deployment dilation devices disclosed herein may have a first pre-deployment diameter that is substantially the same as or close to the diameter of an inner portion of the delivery device. They may also have a second deployment diameter that is larger than the first pre-deployment diameter. Once positioned within the intraluminal device, the post deployment dilation device may be radially expanded to push outwardly on the inner surface of the intraluminal device. Stated differently, the post deployment dilation device is configured such that at least a portion of the post deployment dilation device contacts at least a portion of the inner surface of an intraluminal device and applies a radial force to that inner surface of the intraluminal device. By the application of an outward or radial force to the inside of the intraluminal device (i.e., at least a portion of the inner surface of the intraluminal device), the post deployment dilation device may cause the intraluminal device to expand even further and/or seat more evenly against the surface of the volume in which it is contained (e.g., the blood vessel). After the post deployment dilation device has expanded to exert and outward/radial force on the intraluminal device, it may be contracted or compressed so that it may be moved out from underneath (e.g., withdrawn) from within the intraluminal device without entanglement with the intraluminal device.

A delivery device 10 may include only one, or multiple, post deployment dilation devices. When only one post deployment dilation device is included, the post deployment dilation device may be located distal of the first delivery platform, between a first and second delivery platform, underneath a delivery platform, or even proximal to all delivery platforms. A delivery device delivery device 10 may include more than one post deployment dilation device, for example, two, three, four, five, or six, post deployment dilation devices. When more than one post deployment dilation device is included, the post deployment dilation devices may be located distal and proximal to the delivery platforms, between two or more of the delivery platforms, or within two or more of the delivery platforms.

As described elsewhere herein, the delivery device 10 may be operated/actuated at its proximal end, for example to withdraw the outer sheath 12 and deploy one or more tacks 2. In much the same way, the post deployment dilation devices disclosed herein may be actuated from the proximal end of the delivery device 10. That way, an operator may insert the delivery device 10 into a volume, e.g., a patient's blood vessel, advance the delivery device 10 to a target site, withdraw the outer sheath 12, deploy a tack 2, and use the post deployment dilation device, all from the proximal end of the delivery device 10.

At least some embodiments of the post deployment dilation device include a plurality of expansion filaments 1710, 1910 as shown in FIGS. 8A-10F. As will be explained in more detail below, the expansion filaments can take many forms, such as being free floating or fixed with respect to either the proximal or the distal end of the post deployment dilation device. The expansion filaments can be pre-bent, formed or shaped so that when expanded they can assume a cylindrical shape or other shape consistent with the desired shape of the vessel(s). For example, as shown in FIG. 8F, the expansion filaments 1710 have two bends on each end to collectively form end caps that connect to longitudinal sections that are parallel with the longitudinal axis of the inner shaft.

When fixed with respect to the distal end of the post deployment dilation device (FIGS. 8A-8G), the expansion filaments 1710 may be pushed or extended distally toward the distal end of the post deployment dilation device. Such pushing or extension can cause the expansion filaments to bow, or buckle outwards. Additional pushing or extension of the expansion filaments can cause the expansion filaments to bow or buckle even further outwards. When the post deployment dilation device is inside an intraluminal device, the expansion filaments can be pushed or extended far enough that they contact and exert an outward or radial force on the intraluminal device (as discussed above). Once the post deployment dilation device has been used (e.g., exerted a radial force on the inner surface of the intraluminal device), the expansion filaments may be retracted. Retraction of the expansion filaments can cause them to lie flat against the delivery device 10 so that the delivery device 10 may be withdrawn without getting caught on the intraluminal device.

Alternatively, the expansion filaments 1910 may be fixed with respect to the proximal end of the post deployment dilation device (FIGS. 10A-10F). When fixed with respect to the proximal end of the post deployment dilation device, the expansion filaments may be fixed at their distal ends to a slidable structure, for example, a ring 1920. When the slidable structure is slid (pulled or drawn) toward the proximal end of the delivery device 10 (also toward the proximal fixation points of the expansion filaments), the expansion filaments are caused to bow or buckle outwards. Additional proximal sliding of the slidable structure causes the expansion filaments to bow or buckle even further outwards. If the post deployment dilation device is inside an intraluminal device, the slidable structure can slide proximally far enough so that the expansion filaments bow outward to contact and exert an outward or radial force on the intraluminal device (as discussed above). Once the post deployment dilation device has been used (e.g., exerted a radial force on the inner surface of the intraluminal device), the slidable structure may be pushed distally. Pushing the slidable structure distally causes the expansion filaments to lie flat against the delivery device 10 so that the delivery device 10 may be withdrawn without getting caught on the intraluminal device. Only one expansion filament-based post deployment dilation device may be included. However, more than one may be included (e.g., one set of expansion filaments incorporated into each delivery platform).

In some embodiments, the expansion filaments 1910 can be positioned within a lumen in the inner member and distal movement of the ring 1920 can withdraw the filaments 1910. The filaments 1910 can then assume a pre-bent or shaped expanded form to further expand the intraluminal device.

Another post deployment dilation device disclosed herein includes a flexible bellow (FIGS. 11A-11F). Such flexible bellows may have a first configuration in which the bellow is extended and lies substantially flat against the delivery device 10. They may also have a second configuration in which the bellow is shortened or contracted or expanded. When in its second configuration, the bellow may have a diameter larger than when in its first configuration. Some of the bellows disclosed herein are shaped like an accordion so that when fully extended (in their pre-deployment configuration) they lie substantially flat. However, retraction of these bellows can cause them to fold on themselves, like an accordion. This accordion-like action causes the diameter of the bellow to increase as it is shortened. These bellows may be fixed with respect to the proximal end of the post deployment dilation device (i.e., the proximal end of the bellow is fixed with respect to the proximal end of the post deployment dilation device), the distal end of the post deployment dilation device (i.e., the distal end of the bellow is fixed with respect to the distal end of the post deployment dilation device), or, alternatively, both the proximal and distal end of the bellow may be independently movable. Only one bellow-based post deployment dilation device may be included. However, more than one may be included (e.g., one bellow incorporated into each delivery platform).

Still other post deployment dilation devices disclosed herein include an inflatable balloon (e.g., an inner core balloon 2110, FIGS. 12A-12F). Such balloons may have a pre-deployment configuration having a first diameter which allows the balloon to lie close to an inner portion of the delivery device 10 (such that the outer sheath 12 may fit over the balloon). The balloons may also have a deployment configuration having a second diameter in which the balloon is inflated. As will be readily understood, when placed inside a substantially fixed volume, additional inflation of the balloon will cause additional radial or outward pressure on the inner surface of the volume. Only one balloon-based post deployment dilation device may be included. However, more than one may be included (e.g., one balloon incorporated into each delivery platform). The inflatable balloon can also be used to deliver drugs or biologic therapies to the vessel wall.

One or more embodiment incorporating a balloon into the post deployment dilation device also includes a helical coil 2330 (FIG. 14B) to trap the balloon in its pre-deployment configuration. The helical coil 2330 may be extended from and retraced into a helical coil lumen 2320 (FIG. 14A). Retracting the helical coil into a lumen can cause it to release the balloon so that the balloon may be inflated. Extending the helical coil from a lumen can cause it to wrap helically around the balloon to trap it next to an inner portion of the delivery device 10. So trapping the balloon with the helical coil may be particularly useful after the balloon has been used once (e.g., placed within an intraluminal device, inflated to deploy the intraluminal device, and deflated). Without the helical coil, the deflated balloon may catch on biological structures or the intraluminal device. However, the helical coil can cause the balloon to, once again, lie close against an inner portion of the delivery device.

FIGS. 8A-8G illustrate a delivery device 10 incorporating an embodiment of a post deployment dilation device. More specifically, the delivery system comprises an integrated distal expansion element used to dilate the implants after deployment to ensure ideal apposition between the implant and the vessel wall. Similarly to the delivery device 10 shown in FIG. 7A, the delivery device 10 shown in FIG. 8A includes an outer sheath 12 in a first pre-deployment position. As has been described, multiple tacks 2 can be held by the outer sheath 12 in a compressed state within the delivery device 10 and can extend over a given length of the delivery device. The delivery device 10 includes a guidewire lumen 40 which can extend over a guidewire 50 so that the delivery device 10 can be advanced over the guidewire 50 in a patient's vasculature to a treatment site. As has already been described, the guidewire 50 can be the same guidewire used in prior steps of a procedure. The outer sheath 12 can be withdrawn or retracted to second pre-deployment position (shown in FIGS. 7B and 7C). In the second pre-deployment position, the distal end 52 of the outer sheath can be positioned at, or slightly distal of the distal end of a tack to be deployed.

Like the systems shown in prior figures, the outer sheath 12 can have a radiopaque annular marker band 28 and the tack can also have one or more radiopaque markers 22. The radiopaque markers 22 can be positioned in a column around the tack. Having corresponding radiopaque markers 22, 28 on the tack and the outer sheath can allow the physician to align the markers 22, 28 prior to deployment of the tack as shown in FIG. 8C. Furthermore, the aligned markers may be aligned with the desired area to be treated. Alignment can be accomplished using standard visualization techniques. As has been mentioned, the annular pusher bands 44 on the inner shaft can also be radiopaque.

With reference to FIG. 8B, it can be seen that the marker 28 on the outer sheath 12 and the markers 22 on the first tack 2 are aligned and that the distal end of the sheath is positioned at the distal end of the first tack. The delivery device 10 can now be positioned with respect to the lesion for treatment, such as by centering the radiopaque markers at desired location. The sheath can then be withdrawn to place the tack in the desired location. In addition to positioning the outer sheath 12 such that the tack 2 may be deployed, aligning the radiopaque marker band(s) 28 on the outer sheath 12 with the markers 22 on the first tack 2 exposes a first platform incorporating a post deployment dilation device.

FIGS. 8B and 8C illustrate the post deployment dilation device in a collapsed state. The post deployment dilation device includes a distal radiopaque ring 1720, a proximal radiopaque ring 1722, and a plurality of expansion filaments 1710. Distal radiopaque ring 1720 is generally positioned at or close to the distal end of the post deployment dilation device's platform. By extension, proximal radiopaque ring 1722 is generally positioned at or close to the proximal end of the post deployment dilation device's platform. The post deployment dilation device shown in FIG. 8 has a streamlined pre-deployment configuration and a deployment configuration, which will be discussed in further detail below. FIGS. 8B and 8C show the post deployment dilation device in its pre-deployment configuration.

As mentioned above, the post deployment dilation device includes a plurality of expansion filaments 1710. The expansion filaments 1710 can form a frame. In some embodiments, the post deployment dilation device has 3 expansion filaments 1710. In other embodiments, the post deployment dilation device has distal end 4, 5, 6, 7, 8, 9, 10, 11, or 12 expansion filaments 1710. On still other embodiments, the post deployment dilation device has more than 12 expansion filaments 1710. The expansion filaments 1710 are fabricated out of a flexible material that retains enough rigidity that it can push radially outward, as will be discussed below. In some embodiments, the expansion filaments 1710 are made out of a polymer. In other embodiments, the expansion filaments 1710 are made out of a metal, such as a superelastic metal (e.g., nitinol). The distal portion of each expansion filament 1710 can be pre-shaped to allow for optimal engagement with the inner surface of an implant and subsequent expansion of the implant. In some embodiments, each expansion filament 1710 is covered by a thin, flexible polymer film. This may advantageously help distribute the expansion forces more equally over the surface area of the intravascular device. The polymer film may also help mitigate the potential for entanglement of the filaments into the structure of the intravascular device during dilation. The polymer film can also be used to deliver drugs or biologic therapies to the wall of the blood vessel. Alternatively, in other embodiments, the expansion filaments 1710 may be embedded in the wall of a very fine, very flexible, continuous, expandable structure, such as a balloon. Being so embedded advantageously prevents the expansion filaments 1710 from becoming entangled with and/or caught on the struts or anchors of the tack 2 that is being deployed.

As illustrated, the distal portion of each expansion filament 1710 in the plurality of expansion filaments 1710 is fixed with respect to the inner shaft 26 near the distal end of the post deployment dilation device's platform (e.g., near the distal radiopaque ring 1720). They are fixed in approximately equal divisions around the delivery device 10. For example, in an embodiment in which the post deployment dilation device has only 3 expansion filaments 1710, each expansion filament 1710 is separated from the next expansion filament 1710 by about 120°. In the same way, in an embodiment of the delivery device 10 in which the post deployment dilation device has 6 expansion filaments 1710, each expansion filament 1710 is separated from the next expansion filament 1710 by about 60°.

The expansion filaments 1710 extend proximally from their attachment points with respect to the inner shaft 26, over the post deployment dilation device's platform, and underneath the annular marker bands 44 and the various delivery platforms 8, to a proximal end of the delivery device 10. The various expansion filaments 1710 may each, individually extend all the way to a proximal end of the delivery device 10. Alternatively, the various expansion filaments 1710 may join together, proximal of the post deployment dilation device's platform, to form a single cable that extends proximally to the proximal end of the delivery device 10. A proximal portion of each expansion filament 1710 (or, as just discussed, the single cable comprising each and every expansion filament 1710), is fixed to an expansion control 1730 at the proximal end of the delivery device 10 that may be actuated by a user, e.g., the physician.

In some embodiments, the inner shaft 26 is extruded to include a plurality of lumens through which the expansion filaments 1710 may travel from the post deployment dilation device to the proximal end of the delivery device 10. The inner shaft 26 may consist of a multi-lumen extrusion as shown in FIG. 9A. FIG. 9A illustrates a cross-section of inner shaft 26 having a guidewire lumen 40 at its center as well as six individual filament lumens 1810 within its wall, substantially parallel to the guidewire lumen 40. An expansion filament 1710 may be run from the post deployment dilation device all the way to the proximal end of the delivery device 10, through these filament lumens 1810. The filament lumens 1810 generally provide support and coaxial containment for the multiple expansion filaments 1710 that extend through the filament lumens 1810 from a proximal to distal portion of the delivery device 10.

As will be readily understood, the inner shaft 26 may include any number of filament lumens 1810, including 3 filament lumens 1810. In some embodiments, the inner shaft 26 has 4, 5, 6, 7, 8, 9, 10, 11, or 12 filament lumens 1810. In yet other embodiments, the inner shaft 26 has more than 12 filament lumens 1810. Each filament lumen 1810 may contain an expansion filament 1710. For example, an inner shaft 26 may be extruded with a certain number of filament lumens 1810 (e.g., 8 filament lumens 1810) then the same number of expansion filaments 1710 (i.e., 8 expansion filaments 1710) are inserted into the filament lumens 1810. Such 1:1 ratios may be useful for highly tailored systems. However, by contrast, some of the extruded filament lumens 1810 may remain empty. For example, an inner shaft 26 may be extruded with a comparatively large number of filament lumens 1810 (e.g., 12 filament lumens 1810). Then, only the desired number of expansion filaments 1710 (e.g., 6 expansion filaments 1710) are inserted into the filament lumens 1810. This type of system is more modular and may decrease manufacturing costs as a single extruded inner shaft 26 may accommodate various numbers of expansion filaments 1710.

As shown in FIG. 9B, the expansion filaments 1710 may exit the filament lumens 1810 to extend across the surface of the post deployment dilation device's platform (e.g., the outer surface of the inner shaft 26). In some embodiments, the distal section of the multi-lumen extrusion having the filament lumens 1810 incorporates several longitudinally oriented openings, or pockets, in the wall of the extrusion (e.g., one opening or pocket for each filament lumen 1810). The windows or pockets are generally aligned with a distal portion of the filament lumens 1810 in the inner core multi-lumen extrusion to enable exposure of a distal portion of the expansion filaments 1710 (e.g., the expansion filaments 1710 may exit these windows to travel across the surface of the post deployment dilation device's platform to their respective attachment points). Alternatively, as shown in FIG. 9B, the expansion filaments 1710 may reside in a plurality of filament recesses 1820, which are essentially open-top extensions of the filament lumens 1810. Using such filament recess 1820 may advantageously save space, prevent the expansion filaments 1710 from interacting with each other, and prevent binding and/or excessive friction between the outer sheath 12, expansion filaments 1710, and the inner shaft 26.

In some embodiments, the expansion filaments 1710 can exit the filament lumens 1810 adjacent to a pusher band 44. In this way the pusher band 44 can be used to increase the rigidity and structural integrity of the inner member 26. The nose cone 38 can also be used in this manner. For example, metal radiopaque marker bands in the pusher band 44 and in the nose cone 38 can surround the filament lumens 1710 adjacent the exits locations of the expansion filaments. This can help the delivery device deal with the increased stress on the inner member when the expansion filaments are in the expanded position. As has been mentioned, the pusher band and nose cone can define the respective proximal and distal ends of the post deployment dilation device.

As illustrated, in the post deployment dilation device's pre-deployment state, each expansion filament 1710 lies substantially flat against the inner shaft 26 (or in a filament recess 1820 of the inner shaft 26). In the pre-deployment state, there is little, if any, slack in each expansion filament 1710. That is to say that the length of the expansion filament 1710 between its fixation point at the distal end of the post deployment dilation device's platform and the distal end of the filament lumen 1810 is about the same as the length of the post deployment dilation device's platform.

Activation of the expansion mechanism causes the distal advancement of the filaments through the lumens, which further results in the radial expansion of a distal portion of the filaments through the openings in the wall of the extrusion. Deployment (i.e., activation of the expansion mechanism) is accomplished by pushing on the proximal ends of the various expansion filaments 1710 (or the cable formed by the various expansion filaments 1710). This causes the expansion filament 1710 to extend out of the distal end of its filament lumen 1810 (e.g., distal advancement of the filaments through the lumens), thereby resulting in an extension and radial expansion of a distal portion of the expansion filaments 1710 through the filament lumens 1810, which further results in the radial expansion of a distal portion of the filaments through the openings in the wall of the extrusion. Extension of the distal portion of an expansion filament 1710 increases the length of the expansion filament 1710 between the attachment point at the distal end of the post deployment dilation device and the distal end of the filament lumen 1810. As the length of the expansion filament 1710 above the post deployment dilation device increases, it will "buckle" outward. Pushing more of the expansion filament 1710 out of the filament lumen 1810 causes the expansion filament 1710 to buckle even further outward. That is to say, the expansion diameter of the expansion filaments 1710 is controlled by the longitudinal displacement of the proximal end of the expansion filaments 1710.

FIGS. 8D-8G illustrate a method of using the post deployment dilation device just discussed. In FIG. 8D, the outer sheath 12 has been retracted as discussed elsewhere herein. The radiopaque marker band(s) 28 has been retracted until it overlies the radiopaque markers 22, ready to deploy the second tack 2. As can be seen, the first self-expanding tack 2 has expanded to be substantially apposed to the intraluminal wall. When contained by the outer sheath 12, the tack's 2 radiopaque markers 22 are generally close together, in a tightly packed ring. By contrast, expansion of the tack 2 causes the radiopaque markers 22 to also expand outward, thereby forming a more disperse ring. Therefore, the physician, using standard imaging techniques as discussed elsewhere herein, may observe the tack 2 unseating from its delivery platform 8 and expanding within the vessel. During deployment of the individual self-expanding implants (e.g., tacks 2), the filaments are completely contained within the pockets/recesses and the inner core wall.

Once the tack 2 has been deployed to its target location and stopped expanding within the vessel (i.e., no more or very little motion of the radiopaque markers 22 is observed), the delivery device 10 is moved either proximally or distally and repositioned such that the post deployment dilation device is moved underneath the tack 2, shown in FIG. 8E. In this position, the centers of the exposed distal ends of the expansion filaments 1710 are located at the approximate center of the deployed implant.

A portion of the inner shaft 26 or a portion of the expansion filaments 1710, can include one or more radiopaque elements to allow for optimal longitudinal alignment of the expansion filaments 1710 within the deployed implant. For example, the post deployment dilation device may incorporate the distal radiopaque ring 1720 and the proximal radiopaque ring 1722, which can be used to center the post deployment dilation device within the center of the tack 2. The distal radiopaque ring 1720 and the proximal radiopaque ring 1722 can be observed using conventional imaging techniques, just like the radiopaque markers 22. Consequently, the physician may advance or retract the delivery device 10 until the radiopaque markers 22 lie substantially in the middle of the distal radiopaque ring 1720 and the proximal radiopaque ring 1722. At that point, the tack 2 will be in approximately the center of the post deployment dilation device—the proper location for activation of the post deployment dilation device.

When the post deployment dilation device is centered under the implant, the expansion mechanism may be activated by pushing distally on the proximal ends of the expansion filaments 1710, or the proximal end of the cable comprising the expansion filaments 1710, at the proximal end of the expansion filament 1710. As described above, this causes expansion of each expansion filament 1710 out of its distal sectioned pocket or recess. The radial expansion of the expansion filaments 1710, or "buckling," causes the filaments to engage with the inner surface of the vascular implant, as shown in FIG. 8F. As the expansion filaments 1710 continue to expand radially, they continue to push radially outward on the inner surface of the vascular implant, thereby fully dilating the deployed implant against the inner wall of the vessel.

Following radial expansion of the expansion filaments 1710 and complete deployment of the tack 2, the expansion mechanism can be deactivated by pulling proximally on the proximal ends of the expansion filaments 1710, or the proximal end of the cable comprising the expansion filaments 1710, at the proximal end of the expansion filament 1710. As described above, this causes each expansion filament 1710 to retract back into its distal sectioned pocket or recess, to once again lie flat against the inner shaft 26, shown in FIG. 8G.

While the post deployment dilation device shown in FIGS. 8A-8F was described as being located at the distal end of the delivery device 10, between the tip 38 and the distalmost tack 2, it should be understood that a plurality of such post deployment dilation device may be included in the delivery device 10. For example, one post deployment dilation device (e.g., plurality of expansion filaments 1710) may be incorporated under each tack 2, e.g., into the platform underlying the tack 2. In such embodiments, each post deployment dilation device may have controls accessible at the proximal end of the delivery device 10. Therefore, a user may retract the outer sheath 12 to deploy a tack 2, and, without moving the delivery device 10, activate the post deployment dilation device underlying the tack 2 to post-dilate the implant.

FIGS. 8A-8G illustrate a delivery device 10 having a post deployment dilation device incorporating expansion filaments 1710 that are fixed at the distal end of the post deployment dilation device and translatable/extendable with reference to the proximal end of the post deployment dilation device (and the delivery device 10 as a whole). The delivery device 10 of FIGS. 10A-10F is very similar to the delivery device 10 of FIGS. 8A-8G. However, in FIGS. 10A-10F the proximal ends of the expansion filaments 1910 are fixed to the proximal end of the post deployment dilation device. And, it is the distal ends of the expansion filaments 1910 that translate to cause radial expansion of the expansion filaments 1910.

FIGS. 10A-10C show the post deployment dilation device in various stages of deployment: FIG. 10A illustrates the post deployment dilation device in a pre-deployment state (i.e., fully collapsed); FIG. 10B illustrates the post deployment dilation device in a state of partial deployment; and FIG. 10C illustrates the post deployment dilation device in a state of substantially full deployment.

The illustrated post deployment dilation device generally includes distal radiopaque ring 1720, a proximal radiopaque ring 1722, and a plurality of expansion filaments 1910. Distal radiopaque ring 1720 and proximal radiopaque ring 1722 may be the same as has already been described with respect to FIG. 8. In some embodiments, the post deployment dilation device has 3 expansion filaments 1910. In other embodiments, the post deployment dilation device has distal end 4, 5, 6, 7, 8, 9, 10, 11, or 12 expansion filaments 1910. On still other embodiments, the post deployment dilation device has more than 12 expansion filaments 1910. The expansion filaments 1910 are fabricated out of a flexible material that retains enough rigidity that they can push radially outward, as will be discussed below. Similar to the expansion filaments 1710 of FIG. 8, the expansion filament 1910 can be made out of a polymer or a super-elastic metal (e.g., nitinol). The distal portion of each expansion filament 1910 can be pre-shaped to allow for optimal engagement with the inner surface of an implant and subsequent expansion of the implant. In some embodiments, each expansion filament 1910 is covered by a thin, flexible polymer film. Alternatively, in other embodiments, the expansion filaments 1910 may be embedded in the wall of a very fine, very flexible, continuous, expandable structure, such as a balloon. Thus, the expansion filaments 1910 can form a frame inside the balloon.

By contrast to FIG. 8, the proximal portion of each expansion filament 1910 in the plurality of expansion filaments 1910 is fixed with respect to the inner shaft 26 near the proximal end of the post deployment dilation device's platform (e.g., near the proximal radiopaque ring 1722). They are fixed in approximately equal divisions around the delivery device 10. For example, in an embodiment in which the post deployment dilation device has only 3 expansion filaments 1910, each expansion filament 1910 is separated from the next expansion filament 1910 by about 120°. In the same way, in an embodiment of the delivery device 10 in which the post deployment dilation device has 6 expansion filaments 1910, each expansion filament 1910 is separated from the next expansion filament 1910 by about 60°. In some embodiments, the proximal ends of the expansion filaments 1910 are attached to the inner shaft 26 at the proximal end of the post deployment dilation device's platform. In other embodiments, the expansion filaments 1910 extend back, some distance, into the wall of the inner shaft 26, such as through filament lumens 1810 as was described with respect to FIG. 9A. In such embodiments, the plurality of expansion filaments 1910 align with radially sectioned pockets (such as the filament lumens 1810 of FIG. 9A) around the circumference of the inner shaft 26 and terminate to a fixed position within the lumens in the wall of the inner shaft 26, proximal to the first crimped tack 2.

The expansion filaments 1910 extend distally from their attachment points with respect to the inner shaft 26, over the post deployment dilation device's platform, and attach to a sliding sleeve 1920. The expansion filaments 1910 may be contained within pockets or recesses, when not deployed, as has already been described. The length of the expansion filaments 1910 (e.g., when straight and unbent) result in the sliding sleeve being positioned in its relative "home" position (e.g., near the distal radiopaque ring 1720) with no preload, shown in FIG. 10A. The sliding sleeve is operatively coupled to an expansion control 1730, such as a retractor, at the proximal end of the delivery device 10. The retractor allows a user to cause the sliding sleeve 1920 to slide, coaxially, along the inner shaft 26. In some embodiments, the retractor may be simply one filament or a series of filaments attached to the sliding sleeve, extending over the surface of the post deployment dilation device's platform, into the wall of the inner shaft 26 (e.g., through filament lumens 1810), and to the proximal end of the delivery device 10.

In operation, the retractor may be pulled proximally, thereby causing the sliding sleeve 1920 to slide proximally along the surface of the inner shaft 26. FIG. 10B shows a sliding sleeve 1920 that has been slid partially in the proximal direction. FIG. 10C shows a sliding sleeve 1920 that has been slid even further in the proximal direction. As has been discussed above, the expansion filaments 1910 have a fixed length. Therefore, sliding the sliding sleeve 1920 proximally, towards the expansion filaments' 1910 points of attachment to the inner shaft 26, causes the expansion filaments 1910 to "buckle" outward. Sliding the sliding sleeve 1920 even further proximally causes the expansion filaments 1910 to buckle even further outward. That is to say, the expansion diameter of the expansion filaments 1910 is controlled by the longitudinal displacement of the sliding sleeve 1920.

FIGS. 10D-10F illustrate a method of using the post deployment dilation device just discussed. In FIG. 10D, the outer sheath 12 has been retracted until the radiopaque marker band(s) 28 overlies the radiopaque markers 22 (i.e., until the delivery device 10 is ready to deploy the second tack 2). As shown in FIG. 10D, the first self-expanding tack 2 has expanded to be substantially apposed to the intraluminal wall. During deployment of the individual self-expanding implants (e.g., tacks 2), the filaments can be completely contained within the pockets/recesses and the inner core wall.

Once the tack 2 has been deployed to its target location and stopped expanding within the vessel (i.e., no more or very little motion of the radiopaque markers 22 is observed), the delivery device 10 is moved either proximally or distally and repositioned such that the post deployment dilation device is moved underneath the tack 2, shown in FIG. 10E. In this position, the centers of the exposed expansion filaments 1910 are located at the approximate center of the deployed tack 2.

Radiopaque markers, e.g., distal radiopaque ring 1720 and proximal radiopaque ring 1722 may be used to align the post deployment dilation device with the tack 2. In some embodiments, the distal radiopaque ring 1720 and the proximal radiopaque ring 1722 are used to align the tack 2 in the center of the post deployment dilation device. In other embodiments, the proximal radiopaque ring 1722 is positioned closer to the radiopaque markers 22 of the tack 2 (shown in FIG. 10E). Placing the proximal radiopaque ring 1722 closer to the radiopaque markers 22 may be useful because the post deployment dilation device's largest deployment diameter is biased toward the proximal radiopaque ring 1722 (by contrast to the systems shown in FIG. 8). As the sliding sleeve 1920 moves proximally, the deployment diameter increases. Consequently, the physician may advance or retract the delivery device 10 until the radiopaque markers 22 lie just distal of the proximal radiopaque ring 1722. At that point, the tack 2 may be located where the deployment diameter is sufficiently large for the tack 2—the proper location for activation of the post deployment dilation device.

When the post deployment dilation device is located in the desired position under the implant, the expansion mechanism may be activated by pulling proximally on the retractor. As described above, this causes the sliding sleeve 1920 to slide proximally and the expansion filament 1910 to radially expand outwards, as shown in FIG. 10E. The radial expansion of the expansion filaments 1910, or "buckling," causes the filaments to engage with the inner surface of the vascular implant, as shown in FIG. 10E. As the expansion filaments 1910 continue to expand radially, they continue to push radially outward on the inner surface of the vascular implant, thereby fully dilating the deployed implant against the inner wall of the vessel.

Following radial expansion of the expansion filaments 1910 and complete deployment of the tack 2, the expansion mechanism can be deactivated by pushing distally on the retractor, e.g., at the proximal end of the delivery device 10. As described above, this causes each expansion filament 1910 to retract back into its distal sectioned pocket or recess, to once again lie flat against the inner shaft 26.

While the post deployment dilation device shown in FIGS. 10A-10F was described as being located at the distal end of the delivery device 10, between the tip 38 and the distalmost tack 2, it should be understood that a plurality of such post deployment dilation device may be included in the delivery device 10. For example, one post deployment dilation device (e.g., sliding sleeve 1920 and plurality of expansion filaments 1910) may be incorporated under each tack 2, e.g., into the platform underlying the tack 2. In such embodiments, each post deployment dilation device may have controls accessible at the proximal end of the delivery device 10. Therefore, a user may retract the outer sheath 12 to deploy a tack 2, and, without moving the delivery device 10, activate the post deployment dilation device underlying the tack 2 to post-dilate the implant.

FIGS. 11A-11F illustrate a delivery device 10 having a post deployment dilation device incorporating a pre-formed expandable frame. The frame can be a bellow. This delivery device 10 is very similar to the delivery device 10 of FIGS. 10A-10G. However, whereas the post deployment dilation device shown in FIG. 10 incorporates a plurality of expansion filaments 1910 attached to a sliding sleeve 1920, the post deployment dilation device of FIG. 11 incorporates the expandable bellows 2010 attached to a sliding ring or sleeve 2020 (similar to the sliding sleeve 1920).

FIGS. 11A-11C show the post deployment dilation device in various stages of deployment: FIG. 11A illustrates the post deployment dilation device in a pre-deployment state (i.e., fully collapsed); FIG. 11B illustrates the post deployment dilation device in a state of partial deployment; and FIG. 11C illustrates the post deployment dilation device in a state of substantially full deployment.

The post deployment dilation device generally includes a bellow 2010. The proximal end of the bellow 2010 is generally attached to the inner shaft 26 near or at the proximal end of the post deployment dilation device's platform. The distal end of the bellow 2010 is attached to a sliding sleeve or ring 2020. The sliding sleeve 2020 may be operatively coupled to an expansion control 1730 or retractor at the proximal end of the delivery device 10. The retractor allows a user to cause the sliding sleeve 2020 to slide, coaxially, along the inner shaft 26. In some embodiments, the retractor is simply a series of filaments attached to the sliding sleeve 2020, extending over the surface of the post deployment dilation device's platform, into the wall of the inner shaft 26 (e.g., through filament lumens 1810), and to the proximal end of the delivery device 10.

The sliding sleeve 2020 may be positioned in its relative "home" position (e.g., near the distal radiopaque ring 1720), shown in FIG. 11A. In some embodiments, some axial force is necessary to hold the sliding sleeve 2020 in its distalmost position. In such embodiments, the retractor may be used to provide such an axial force in the distal direction. In the post deployment dilation device's undeployed state, when the sliding sleeve 2020 lies in its "home" position, the bellow 2010 lies substantially flat against the post deployment dilation device's platform.

In operation, the retractor may be moved proximally, thereby causing the sliding sleeve 2020 to slide proximally along the surface of the inner shaft 26. In some embodiments, the retractor is pulled proximally. However, in other embodiments, the axial force in the distal direction is merely decreased to allow the retractor to move proximally. FIG. 11B shows a sliding sleeve 2020 that has been slid partially in the proximal direction. FIG. 11C shows a sliding sleeve 2020 that has been slid even further in the proximal direction. Sliding the sliding sleeve 2020 proximally, towards the bellow's 2010 point of attachment to the inner shaft 26, causes the bellow 2010 to accordion. As the bellow 2010 accordions, it will move from a substantially straight, sheath configuration, to an accordion-like configuration having a plurality of bellow recesses 2012 and a plurality of bellow ridges 2014 having a bellow diameter 2020. As can be seen with reference to FIGS. 11B and 11C, the bellow diameter 2020 is controlled by the longitudinal displacement of the sliding sleeve 2020. That is to say that as the sliding sleeve 2020 moves even further proximally, the bellow 2010 will accordion even more, causing the bellow diameter 2020 to increase even further. The bellow 2010 can be made of a number of filaments formed into a frame with a cover to create the recesses 2012 and ridges 2014. For example, the filament can be wound in a helical configuration. The frame can be moved so that one end is moved closer to the other to expand the bellows.

FIGS. 11D-11F illustrate a method of using the post deployment dilation device just discussed. The method is substantially the same as the method described with respect to FIGS. 10D-10F. In short, a tack 2 is deployed in the vasculature, then one or more radiopaque markers are used in concert with the radiopaque markers 22 of the tack 2 to align the post deployment dilation device with the tack 2. Once the tack 2 is aligned with the post deployment dilation device as desired, the post deployment dilation device is activated by using the retractor to move the sliding sleeve 2020 in the proximal direction. As the sliding sleeve 2020 moves, the bellow 2010 accordions and increases its bellow diameter such that the bellow ridge 2014 contact the inner surface of the tack 2. As the bellow 2010 continues to expand radially (i.e., the bellow diameter continues to increase), it continues to push radially outward on the inner surface of the vascular implant, thereby fully dilating the deployed implant against the inner wall of the vessel.

While the post deployment dilation device shown in FIGS. 11A-11F was described as being located at the distal end of the delivery device 10, between the tip 38 and the distalmost tack 2, it should be understood that a plurality of such post deployment dilation device may be included in the delivery device 10. For example, one post deployment dilation device (e.g., bellow 2010) may be incorporated under each tack 2, e.g., into the platform underlying the tack 2. In such embodiments, each post deployment dilation device may have controls accessible at the proximal end of the delivery device 10. Therefore, a user may retract the outer sheath 12 to deploy a tack 2, and, without moving the delivery device 10, activate the post deployment dilation device underlying the tack 2 to post-dilate the implant.

FIGS. 12A-12F illustrate another embodiment of a delivery device 10 having a post deployment dilation device incorporating a balloon. FIGS. 12A-12C show the post deployment dilation device in various stages of deployment: FIG. 12A illustrates the post deployment dilation device in a pre-deployment state (i.e., fully collapsed); FIG. 12B illustrates the post deployment dilation device in a state of partial deployment (i.e., only partially inflated); and FIG. 12C illustrates the post deployment dilation device in a state of substantially full deployment (i.e., fully inflated).

The post deployment dilation device generally includes distal radiopaque ring 1720, a proximal radiopaque ring 1722, and an inner core balloon 2110. Distal radiopaque ring 1720 and proximal radiopaque ring 1722 may be the same as has already been described with respect to FIG. 8. The inner core balloon 2110 may be constructed from a compliant elastic material (e.g., silicone, nylon, or polyurethane).

The inner core balloon 2110 may extend from about the distal radiopaque ring 1720 or the distal end of the post deployment dilation device's platform to about the proximal radiopaque ring 1722 or the proximal end of the post deployment dilation device's platform. As illustrated in FIG. 12, the inner core balloon 2110 can be placed on the inner core shaft (e.g., the inner shaft 26), distal to the implants, e.g., the unexpanded tack. 2. However, it should be understood that the inner core balloon 2110 can be placed on the outer sheath 12 using similar construction principles.

In some embodiments, the inner core balloon 2110 has a pre-deployment diameter that is only marginally larger than the inner shaft 26. In such embodiments, the pre-deployment diameter is sufficiently small that the inner core balloon 2110 may reside between the inner shaft 26 and the outer sheath 12. In some embodiments, the inner core balloon 2110 may have a fully expanded diameter of about 8 mm. In other embodiments, the inner core balloon 2110 has an expanded diameter of about 0.4, 0.6, 0.8, 1, 1.2, 1.4, 1.6, 1.8, 2, 2.2, 2.4, 2.6, 2.8, 3, 3.2, 3.4, 3.6, 3.8, 4, 4.2, 4.4, 4.6, 4.8, 5, 5.2, 5.4, 5.6, 5.8, 6, 6.2, 6.4, 6.6, 6.8, 7, 7.2, 7.4, 7.6, 7.8, 8, 8.2, 8.4, 8.6, 8.8, 9, 9.2, 9.4, 9.6, 9.8, or 10 mm. In other embodiment, the 2110 has any other expanded diameter that is appropriate for fully deploying a vascular device within a subject's vasculature.

The inner core balloon 2110 can be inflated by a fluid transferred from the proximal end of the delivery device 10 to the inner core balloon 2110 through one or more lumens. In some embodiments, the inner shaft 26 is extruded to include one or more lumens through which fluids may travel from one end of the delivery device 10 to the other. The inner shaft 26 may consist of a multi lumen extrusion as shown in FIG. 13, which illustrates an inner shaft 26 having a guidewire lumen 40 at its center as well as two fluid lumens 2220 within its wall, substantially parallel to the guidewire lumen 40. Fluid (e.g., a gas or a liquid fluid) may be pumped from the proximal end of the delivery device 10 to the distal end of the delivery device 10. For example, fluid may be pumped from the proximal end of the delivery device 10 to the post deployment dilation device of FIGS. 12A-12F to inflate the inner core balloon 2110.

As will be readily understood, while two fluid lumens 2220 are shown, the inner shaft 26 may include only 1 fluid lumen 2220. In some embodiments, the inner shaft 26 include 3, distal end 4, 5, 6, 7, or even 8 fluid lumens 2220. In other embodiments, the inner shaft 26 includes more than 8 fluid lumens 2220.

In operation, as shown in FIGS. 12A-12F, fluid may be pumped into the inner core balloon 2110 from the proximal end of the delivery device 10, thereby causing the inner core balloon 2110 to inflate. Various amount of fluid pumped or injected into the inner core balloon 2110 can cause various amounts of radial pressure on the walls of the inner core balloon 2110. FIG. 12A shows the inner core balloon 2110 in its pre-deployment state, almost completely collapsed against the inner shaft 26. FIG. 12B shows an inner core balloon 2110 that has been only partially inflated. Finally, FIG. 12C shows an inner core balloon 2110 that has been fully inflated. Ultimately, expansion of the inner core balloon 2110 is controlled by the amount of fluid pumped into the inner core balloon 2110. In some embodiments, the delivery device 10 includes a pressure sensor capable of detecting the pressure within the inner core balloon 2110. In such embodiments, the pressure sensor may advantageously communicate with the pump (that is pumping the fluid from the proximal end of the delivery device 10 into the inner core balloon 2110) such that the pump may automatically stop pumping before the burst pressure of the inner core balloon 2110 is reached.

FIGS. 12D-12F illustrate a method of using the post deployment dilation device just discussed. In FIG. 12D, the outer sheath 12 has been retracted until the radiopaque marker band(s) 28 overlies the radiopaque markers 22 (i.e., until the delivery device 10 is ready to deploy the second tack 2). As shown in FIG. 10D, the first self-expanding tack 2 has expanded to be substantially apposed to the intraluminal wall. During deployment of the individual self-expanding implants the inner core balloon 2110 is completely deflated against the outer diameter of the inner shaft 26.

Once the tack 2 has been deployed to its target location and stopped expanding within the vessel (i.e., no more or very little motion of the radiopaque markers 22 is observed), the delivery device 10 is moved either proximally or distally and repositioned such that the post deployment dilation device is moved underneath the tack 2, shown in FIG. 12E. In this position, the center of the inner core balloon 2110 is located at the approximate center of the deployed tack 2.

Radiopaque markers, e.g., distal radiopaque ring 1720 and proximal radiopaque ring 1722 may be used to align the post deployment dilation device with the tack 2 as discussed above. In some embodiments, the distal radiopaque ring 1720 and the proximal radiopaque ring 1722 are used to align the tack 2 in the center of the post deployment dilation device. In other embodiments, the proximal radiopaque ring 1722 is positioned closer to the radiopaque markers 22 of the tack 2.

When the post deployment dilation device is located in the desired position under the implant, the inner core balloon 2110 may be inflated by pumping fluid from the proximal end of the delivery device 10, through the one or more fluid lumens 2220, and into the inner core balloon 2110. As described above, this causes the inner core balloon 2110 to radially expand outwards, as shown in FIG. 12E (showing partial expansion) and FIG. 12D (showing nearly complete expansion). The radial expansion of the inner core balloon 2110 causes the outer surface of the inner core balloon 2110 to engage with the inner surface of the vascular implant, as shown in FIG. 12E. As the inner core balloon 2110 continues to radially expand, it continues to push radially outward on the inner surface of the vascular implant, thereby fully dilating the deployed implant against the inner wall of the vessel.

Following radial expansion of the inner core balloon 2110 and complete deployment of the tack 2, the expansion mechanism can be deactivated by deflating the inner core balloon 2110, e.g., by removing the expansion fluid. In some embodiments, the expansion fluid is removed actively, such as by pumping the fluid out. In other embodiments, the expansion fluid is removed passively, such as by simply opening a purge valve and allowing the expansion to flow out due to the pressure differential that exists. As described above, deflating the inner core balloon 2110 causes the balloon to retract (e.g., due to elastic properties of the inner core balloon 2110) and to once again lie flat against the inner shaft 26.

While the post deployment dilation device shown in FIGS. 12A-12F was described as being located at the distal end of the delivery device 10, between the tip 38 and the distalmost tack 2, it should be understood that a plurality of such post deployment dilation device may be included in the delivery device 10. For example, one post deployment dilation device (e.g., inner core balloon 2110) may be incorporated under each tack 2, e.g., into the platform underlying the tack 2. In such embodiments, each post deployment dilation device may have controls accessible at the proximal end of the delivery device 10. Therefore, a user may retract the outer sheath 12 to deploy a tack 2, and, without moving the delivery device 10, activate the post deployment dilation device underlying the tack 2 to post-dilate the implant.

To help confine the inner core balloon 2110 against the inner shaft 26, both before and after use of the post deployment dilation device to deploy a tack 2, a helical filament 2330 may be used. The helical filament 2330 may be an elongate filament having a helical distal end and a long, substantially straight, proximal portion. The helical distal end of the helical filament 2330 need be helical only in the region of the post deployment dilation device and the inner core balloon 2110, as shown in FIG. 14B. The rest of the helical filament 2330 may be straight, extending back through the inner shaft 26 to the proximal end of the delivery device 10.

FIG. 14A illustrates an inner shaft which has been extruded to include multiple lumens, including a guidewire lumen 40 at its center, two fluid lumens 2220 and a helical filament lumen 2320 (shown containing the helical filament 2330). The helical filament 2330 may extend from the post deployment dilation device's platform all the way back to the proximal end of the delivery device 10 through the helical filament lumen 2320.

The helical filament 2330 is preferably made out of a flexible material that retains enough rigidity that it can regain its shape after deformation, as will be discussed below. In some embodiments, the helical filament 2330 is made out of a polymer. In other embodiments, the helical filament 2330 is made out of a metal, such as a super-elastic metal (e.g., nitinol).

In its pre-deployment state, shown in FIG. 14B, the helical filament 2330 is helically wound around the inner core balloon 2110. After the tack 2 has been deployed and the post deployment dilation device centered under the deployed tack 2, the helical filament 2330 may be retracted from over the inner core balloon 2110 using one or more of a proximal pulling and a twisting motion to withdraw the helical filament 2330 into the helical filament lumen 2320.

As the helical filament 2330 is withdrawn into the helical filament lumen 2320, its helical distal portion will elastically deform. When the helical filament 2330 is fully withdrawn from over the inner core balloon 2110, the inner core balloon 2110 may be used as described above.

Following use of the inner core balloon 2110, the inner core balloon 2110 is deflated as described above. Then, the helical filament 2330 can be used to capture and contain the outer diameter of the post-deflated inner core balloon 2110 to minimize the inner core balloon 2110's crossing profile, thereby mitigating potential interactions between an irregularly shaped post-deflated inner core balloon 2110 and deployed implants (e.g., tacks 2) and the vessel. To re-capture the inner core balloon 2110, the helical filament 2330 is extended back out of the helical filament lumen 2320 using one or more of a distal pushing and a twisting motion. As the helical distal portion of the helical filament 2330 extends out of the helical filament lumen 2320, it regains its shape, due to its elastic properties, and helically wraps around the deflated inner core balloon 2110 to confine the inner core balloon 2110 and minimize its deflated crossing profile (shown in FIG. 14B). Some embodiments of the helical filament 2330 include a rounded or blunted distal tip to prevent snagging and/or catching on the material of the inner core balloon 2110.

After the helical filament 2330 has been extended back out of the helical filament lumen 2320, the delivery device 10 may be moved proximally or distally to post-dilate another implant. Because the helical filament 2330 confines the inner core balloon 2110, risk of interactions between the irregularly shaped post-deflated inner core balloon 2110 and other structures may be mitigated. Once the post deployment dilation device and inner core balloon 2110 have been position at a desired location relative to another implant (e.g., tack 2), the helical filament 2330 may be retracted into the helical filament lumen 2320 thereby allowing inflation of the inner core balloon 2110. This process may be repeated for successive post-dilations of multiple implants.

In another embodiment, rather than retract the helical filament 2330, the helical filament 2330 can be advanced out of the lumen 2320 to increase its size. Alternatively, filling the balloon 2110 can force the helical filament 2330 to expand with the balloon, pulling the filament out of the lumen 2320. Removing the fluid can allow the helical filament to cinch down on the balloon, retracting itself into the lumen as the balloon decreases in size.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A delivery device comprising:
    an inner shaft;
    a distal annular band and a proximal annular band fixed to the inner shaft;
    a delivery platform between the distal annular band and the proximal annular band, wherein the delivery platform is configured to receive a self-expanding intraluminal device for deployment from the delivery device into a vessel;
    an outer sheath slidable over the inner shaft and the delivery platform, the outer sheath having a pre-deployment position covering the delivery platform, and at least one delivery position uncovering the delivery platform and at least one of the distal annular band and the proximal annular band; and
    a post deployment dilation device comprising:
        a deployment platform fixed with respect to the inner shaft;
        a balloon fixed with respect to a longitudinal axis of the deployment platform, the balloon having a pre-actuated position having a pre-deployment diameter and an actuated position having a deployment diameter larger than the pre-deployment diameter;
        at least one inflation fluid lumen in fluid communication with the balloon and extending along at least a portion of the inner shaft;
        a filament lumen; and
        a helical coil extendable from the filament lumen to trap the balloon in the pre-deployment position and retractable from the filament lumen to allow the balloon to be inflated to the actuated position;
    wherein the post deployment dilation device is configured to apply a radial force to an inner surface of the self-expanding intraluminal device after deployment of the self-expanding intraluminal device to improve at least one of expansion of the self-expanding intraluminal device and seating of the self-expanding intraluminal device in the vessel.

2. The delivery device of claim 1, wherein the helical coil comprises an elongate filament having a helical distal portion including a rounded or blunted distal tip and a straight proximal portion, the proximal portion extending to a proximal end of the delivery device.

3. The delivery device of claim 1, wherein the helical coil comprises a flexible material configured to retain shape after deformation.

4. A delivery device comprising:
    an inner shaft configured to receive a self-expanding intraluminal device for deployment from the delivery device into a vessel;
    an outer sheath disposed about at least a portion of the inner shaft and movable with respect to the inner shaft, the outer sheath having a pre-deployment position in which the self-expanding intraluminal device is at least partially covered and at least one delivery position in which the self-expanding intraluminal device is uncovered to release the self-expanding intraluminal device from the delivery device; and a post deployment dilation device comprising:
 a balloon attached to the inner shaft of the delivery device, the balloon having a pre-actuated configuration having a pre-deployment diameter and an actuated configuration having a deployment diameter larger than the pre-deployment diameter; and
 a helical coil configured to trap the balloon in the pre-deployment position;
at least one inflation fluid lumen in fluid communication with the balloon and extending along at least a portion of the inner shaft;
wherein the post deployment dilation device is configured to apply a radial force to an inner surface of the self-expanding intraluminal device after deployment of the self-expanding intraluminal device to improve at least one of expansion of the self-expanding intraluminal device and seating of the self-expanding intraluminal device in the vessel.

5. The delivery device of claim 4, wherein the self-expanding intraluminal device has a deployed diameter range of greater than about 3 mm.

6. The delivery device of claim 4, wherein the balloon has a working diameter range of no less than about 3 mm.

7. The delivery device of claim 4, wherein at least a portion of the outer sheath extends over the balloon when the outer sheath is in the pre-deployment position.

8. The delivery device of claim 4, wherein the outer sheath and the inner tube are movable with respect to each other.

9. The delivery device of claim 4, wherein a cross-sectional shape of the inner shaft and a cross-sectional shape of the outer sheath are similar.

10. The delivery device of claim 4, further comprising a delivery platform between a distal pusher and a proximal pusher, wherein the delivery platform is configured to receive the self-expanding intraluminal device for deployment from the delivery device into the vessel.

11. The delivery device of claim 4, wherein the inner shaft is configured to receive a plurality of intraluminal devices for deployment from the delivery device into the vessel.

12. The delivery device of claim 4, wherein the helical coil comprises an elongate filament having a helical distal portion including a rounded or blunted distal tip and a straight proximal portion, the proximal portion extending to a proximal end of the delivery device.

13. The delivery device of claim 4, further comprising filament lumen and a guidewire lumen, wherein the helical coil is configured to have a helical coil shape out of the filament lumen.

14. An intraluminal device deployment method comprising:
 advancing a delivery device with a self-expanding intraluminal device in a compressed state to a target volume, wherein the delivery device comprises:
  an inner shaft configured to receive the self-expanding intraluminal device for deployment from the delivery device into the target volume;
  an outer sheath disposed about at least a portion of the inner shaft and movable with respect to at least a portion of the inner shaft and having at least one delivery position in which the self-expanding intraluminal device is uncovered to release the self-expanding intraluminal device from the delivery device; and
  a post deployment dilation device comprising a balloon attached to the inner shaft of the delivery device and a helical coil, the balloon configured to be radially expanded upon activation of the post deployment dilation device and to generate an outward radial force on an inner surface of the self-expanding intraluminal device after release and expansion of the self-expanding intraluminal device;
 retracting the outer sheath with respect to the inner shaft to release the self-expanding intraluminal device;
 expanding the self-expanding intraluminal device, wherein the expanding comprises one of allowing the self-expanding intraluminal device to expand and actively expanding the self-expanding intraluminal device;
 moving the delivery device to position at least a portion of the post deployment dilation device within the expanded self-expanding intraluminal device;
 activating the post deployment dilation device to cause at least a portion of the post deployment dilation device to radially expand and to generate an outward radial force on an inner surface of the expanded self-expanding intraluminal device; and
 trapping the balloon in the helical coil.

15. The method of claim 14, further comprising deactivating the post deployment dilation device to cause at least a portion of the post deployment dilation device to radially contract.

16. The method of claim 14, further comprising retracting the delivery device from within the expanded self-expanding intraluminal device.

17. The method of claim 14, wherein the delivery device is configured to hold and deliver a plurality of self-expanding intraluminal devices.

18. The method of claim 17 further comprising:
 repeating the retracting, expanding, moving and activating steps for each self-expanding intraluminal device of the plurality of self-expanding intraluminal devices released in the target volume; and
 removing the delivery device from within the target volume.

19. The method of claim 14, wherein activating the post deployment dilation device comprises adding fluid to the balloon.

20. The method of claim 14, further comprising advancing the outer sheath to cover at least a portion of the balloon of the post deployment dilation device prior to removal of the delivery device from within the target volume.

21. The method of claim 14, wherein trapping the post deployment dilation device in the helical coil is after activating the post deployment dilation device.

22. The method of claim 14, wherein trapping the post deployment dilation device in the helical coil comprises confining the balloon.

23. The method of claim 14, wherein trapping the post deployment dilation device in the helical coil comprises extending the helical coil out of a filament lumen.

24. The method of claim 23, further comprising retracting the helical coil into the filament lumen.

25. The method of claim 23, wherein the helical coil is configured to have a helical coil shape out of the filament lumen.

26. The method of claim 14, wherein the helical coil comprises an elongate filament having a helical distal portion including a rounded or blunted distal tip and a straight proximal portion.

* * * * *